United States Patent [19]
Muchowski et al.

[11] 3,940,407
[45] Feb. 24, 1976

[54] β-ADRENERGIC BLOCKING AGENTS IN THE 1,2,3-THIADIAZOLE SERIES

[75] Inventors: Joseph M. Muchowski, Mexico City, Mexico; John H. Fried, Palo Alto, Calif.

[73] Assignee: Syntex (U.S.A.) Inc., Palo Alto, Calif.

[22] Filed: Sept. 16, 1974

[21] Appl. No.: 506,659

[52] U.S. Cl............. 260/302 D; 260/468 E; 424/270
[51] Int. Cl.² .................................... C07D 285/06
[58] Field of Search ............................. 260/302 D

[56] References Cited
UNITED STATES PATENTS
3,729,469  4/1973  Wasson............................ 260/302 D

*Primary Examiner*—Richard J. Gallagher
*Attorney, Agent, or Firm*—William B. Walker; Lawrence S. Squires

[57] ABSTRACT

Novel 4-[2,3 or 4(3-amino-2-hydroxypropoxy) phenyl]- and 5-[2,3 or 4(3-amino-2-hydroxypropoxy) phenyl]-1,2,3-thiadiazole derivatives which may be further substituted at the C-5 or C-4 position of the thiadiazole ring, respectively, by a lower alkyl, phenyl, trifluoromethyl, carboxy, alkoxycarbonyl, cyano or an aminocarbonyl group, and the pharmaceutically acceptable acid addition salts thereof and processes for the production of such compounds; 4-[4(3-t-butylamino-2-hydroxypropoxy)phenyl]-1,2,3-thiadiazole and 5-[4(3-t-butylamino-2-hydroxypropoxy)phenyl]-1,2,3-thiadiazole are representative of the class. These compounds possess cardiovascular activity and are useful for the treatment of abnormal heart conditions in mammals.

41 Claims, No Drawings

β-ADRENERGIC BLOCKING AGENTS IN THE 1,2,3-THIADIAZOLE SERIES

The present invention relates to substituted 1,2,3-thiadiazole derivatives having valuable pharmacological properties, to methods for producing such compounds and to certain novel intermediates obtained thereby.

More particularly the present invention relates to 4-[2,3 or 4(3-amino-2-hydroxypropoxy)phenyl]- and 5-[2,3 or 4-(3-amino-2-hydroxypropoxy)phenyl]-1,2,3-thiadiazole derivatives represented by the following formulas:

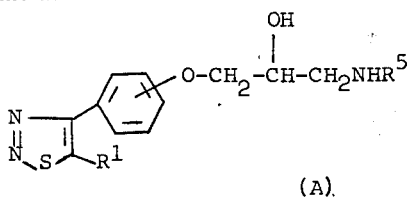

(A)

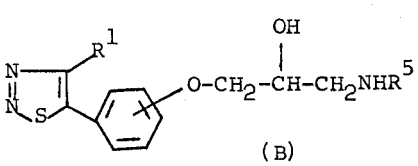

(B)

wherein $R^1$ is a substituent in the thiadiazole ring in either the 4 or 5 position selected from the group consisting of hydrogen, lower alkyl, phenyl, trifluoromethyl, carboxy, lower alkoxycarbonyl, cyano, and an unsubstituted, monosubstituted or disubstituted aminocarbonyl group of the formula $CONR^3R^4$, wherein each of $R^3$ and $R^4$ is independently hydrogen, alkyl having 1 through 8 carbon atoms, aryl or aralkyl;

$R^5$ is hydrogen, lower alkyl, cycloalkyl containing from 3 to 7 carbon atoms, aryl, aralkyl or the group

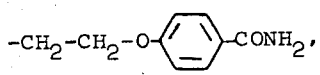

and the group

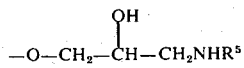

can be situated at the ortho-, meta- or para- positions with respect to the thiadiazole ring. Also encompassed within the invention are the pharmaceutically acceptable acid addition salts of such compounds.

These compounds contain an asymmetric carbon atom in the aminohydroxypropoxy moiety and thus exist as optical isomers, therefore, the above formulas are intended to represent the respective individual (+) and (−) optical isomers as well as mixtures of such isomers. Both the individual isomers and mixtures thereof are encompassed within the scope of the invention.

These novel compounds possess β-adrenergic blocking activities, i.e., they block the action of catecholamines at the adrenergetic β-receptor sites, thus are useful for the treatment of cardiovascular diseases in mammals, as described hereinafter in detail.

At the present time, the compound frequently used in the United States for the treatment of several cardiac arrhythmias is propanolol (i.e., 1-(isopropylamino)-3-(1-naphthyloxy)-2-propanol). This compound primarily achieves its therapeutic action by blocking cardiac β-adrenergic receptor sites and is a general β-adrenergic blocker which blocks the peripheral β-adrenergic receptor sites, such as those in the lung, as well as the β-adrenergic receptor sites in the heart. Propanolol is contraindicated in patients who suffer from asthma or chronic obstructive lung disease, because following its administration to such patients, an increase in airway resistance and bronchial constriction has been observed.

The novel thiadiazole compounds of the present invention represented by formulas (A) and (B) above are β-adrenergic blockers and therefore are effective for the treatment or palliation of angina pectoris and several cardiac arrhythmias. Further a number of these compounds (e.g. 4-[4{3(4-carbamoylphenoxyethylamino)-2-hydroxypropoxy}-phenyl]-1,2,3-thiadiazole) are selective myocardial β-adrenergic blockers and thus can safely be used by patients suffering from asthma or chronic obstructive lung disease.

As used herein above and below, the following terms have the following meanings, unless expressly stated to the contrary. The term "lower alkyl" refers to straight and branched chain alkyl groups having from 1 through 6 carbon atoms, e.g., methyl, ethyl, n-propyl, isopropyl, n-butyl, t-butyl, n-pentyl, n-hexyl, 4-methylpentyl and the like. The term alkyl refers to both straight and branched chain alkyl groups having from 1 to 8 carbon atoms and thus includes, in addition to lower alkyl groups such as illustrated above, 4-methylhexyl, n-octyl, 4-methylhexyl, 5-methylhexyl, 6-methyl-heptyl, 5-methylheptyl, 1-methylheptyl and the like. The term "cycloalkyl" refers to cyclic hydrocarbon groups having from 3 through 7 carbon atoms, such as, for example, cyclopropyl, cyclopentyl, cyclohexyl, cycloheptyl and the like.

The term "lower alkoxy" refers to groups having the formula R′O— wherein R′ is lower alkyl. Typical lower alkoxy groups include, for example, methoxy, ethoxy, propoxy, isopropoxy, t-butoxy and the like.

The terms "lower alkoxycarbonyl or lower carboalkoxy" refer to groups of the formula

in which R′ is lower alkyl. Typical lower alkoxycarbonyl groups include, for example, methoxycarbonyl, ethoxycarbonyl, propoxycarbonyl, isopropoxycarbonyl, n-butoxycarbonyl and the like.

The term "aryl" refers to an aromatic ring having from 6 to 10 carbon atoms, particularly phenyl.

The term "aralkyl" refers to phenyl lower alkyl groups in which "lower alkyl" is as defined above. Typical aralkyl groups are benzyl, phenethyl and the like.

The term "pharmaceutically acceptable acid addition salts" refers to non-toxic, pharmaceutically acceptable salts of the amino group with an inorganic acid such as hydrochloric acid, hydrobromic acid, sulfuric acid, phosphoric acid, etc., or with organic acids such as tartaric acid, lactic acid, maleic acid, citric acid, and the like.

The novel thiadiazole derivatives of formula (A) can be prepared by a process illustrated by the following sequence of reactions:

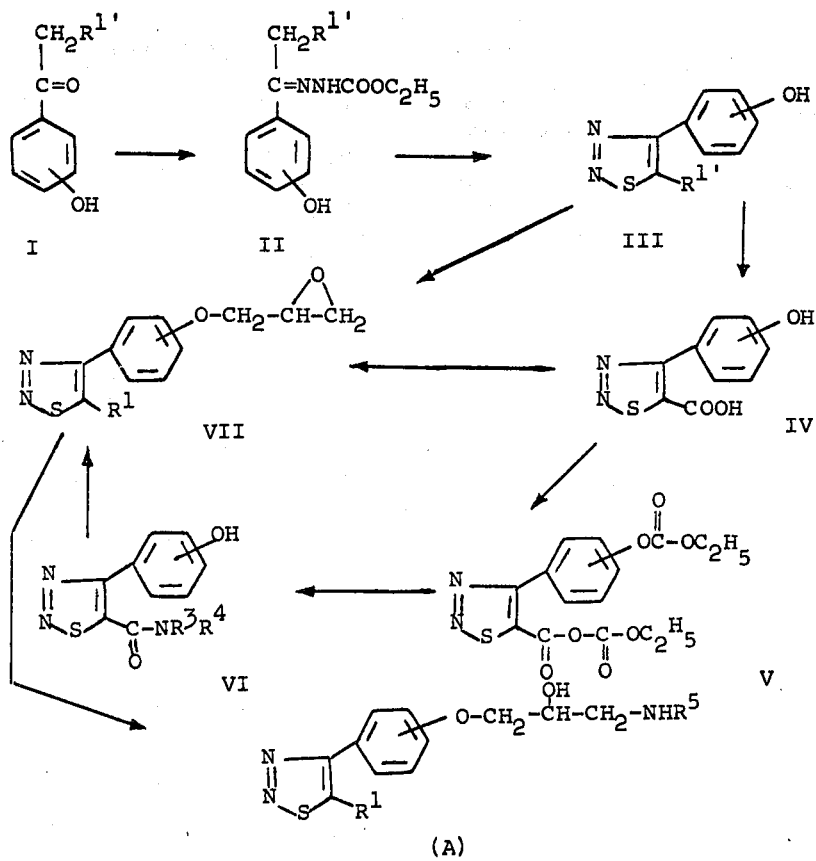

wherein
$R^{1'}$ is hydrogen, lower alkyl, trifluoromethyl, cyano, phenyl or carboethoxy;
$R^1$, $R^3$, $R^4$ and $R^5$ are as defined above.

In practicing the process outlined above, an ortho-, meta- or para-hydroxy substituted phenyl ketone of formula I is condensed with carbethoxyhydrazine in the presence of acetic acid, in a lower aliphatic alcohol as solvent, e.g., methanol or ethanol, to produce the ethoxycarbonylhydrazone of formula II. The reaction is conducted at a temperature comprised between room temperature and reflux, for a period of time sufficient to complete the reaction, of the order of about 3 to about 24 hours, using at least 1.1 molar equivalents of the hydrazine per molar equivalent of compound of formula I. The amount of acetic acid is not critical, thus it can be used from catalytic amounts to a large excess.

By reaction of the ethoxycarbonylhydrazone compounds of formula II with thionyl chloride there are obtained the corresponding 4-(o,m or p-hydroxyphenyl)-thiadiazole intermediates for formula III. This reaction is conducted under anhydrous conditions, using an excess of thionyl chloride, which serves both as reagent and solvent.

In the preferred embodiments, the starting compound of formula II is carefully added to the freshly distilled thionyl chloride, previously cooled to −20° to 0°C, maintaining the reaction mixture at a temperature not higher than room temperature until the evolution of gas ceases. Thereafter the reaction mixture is maintained at a temperature comprised between room temperature and reflux, for about 30 minutes to 24 hours, the reaction time depending upon the temperature at which the reaction takes place and the nature of the starting compound. In general compounds in which $R^{1'}$ is hydrogen, require shorter reaction times or lower temperatures than those in which $R^{1'}$ is other than hydrogen.

The thiadiazole intermediates of formula III are isolated by conventional means, such as evaporation of the excess thionyl chloride and purification of the residue by crystallization or chromatography.

Upon basic hydrolysis of the 5-carboethoxy thiadiazole compounds of formula III ($R^{1'}$ =COOC$_2$H$_5$), using an alkali metal hydroxide, i.e., sodium or potassium hydroxide in an aliphatic alcohol at reflux temperature for about 3 to 5 hours, followed by acidification there are obtained the 5-carboxy thiadiazole derivatives of formula IV. The latter compounds are converted into the aminocarbonyl derivatives of formula VI via formation of the mixed carboxylic-carbonic anhydride of formula V followed by treatment with a primary or secondary amine and hydrolysis of the esterified phenolic hydroxyl group.

Typically, the 5-carboxythiadiazole (IV) is treated with equimolecular quantities of ethyl chlorocarbonate and triethylamine in an inert organic reaction medium, using preferably a mixture of diethyl ether-toluene as solvent. The reaction is conducted at about 0°C for a period of time of about 20 minutes to two hours, to form the mixed carboxyliccarbonic anhydride of formula V, (concomitant esterification of the phenolic hydroxyl group takes place), which is then treated with at least one molar equivalent of a mono- or di-(lower)alkylamine in the same reaction medium, at a temperature comprised between 0°C to room temperature, for a period of time sufficient to complete the reaction. In the preferred embodiments, the carboxylic-carbonic anhydride is treated with the amine at 0°C, in a dropwise fashion, and thereafter the reaction mixture is allowed to attain room temperature and maintained at said temperature overnight. When using one molar equivalent of the amine a basic treatment is necessary to hydrolyze the esterified phenolic hydroxyl group, e.g., brief treatment with sodium carbonate in methanol solution.

When a large excess of amine is used to convert the mixed carboxylic-carbonic anhydrides (V) into the aminocarbonyl compounds of formula VI, i.e., when using from 4 to 10 molar equivalents of the amine, said treatment with sodium carbonate is often not necessary.

Upon reaction of the 4(o, m- or p-hydroxy)-phenylthiadiazole derivatives of formula III, IV and VI with a strong base and thereafter with an epihalohydrin, i.e., epibromohydrin or epichlorohydrin there are produced the 4(o-,m- or p-epoxypropoxy)phenyl thiadiazole compounds of formula VII. This transformation is conducted in aqueous solutions. In the preferred embodiments, the starting compound of formulas III or VI is added to an aqueous solution of an alkali metal hydroxide e.g., sodium or potassium hydroxide, using equimolecular amounts of starting compound and base to readily form the sodium salt, which is immediately treated with 1 to 3 molar equivalents of the halohydrin, using particularly from 1.5 to 2 molar equivalents of epibromohydrin, maintaining the reaction mixture at about room temperature for a period of time of the order of about 15 to 80 hours, preferably for about 20 to 72 hours. When using a compound of formula IV as starting material there are required two molar equivalents of base, besides, when the reaction with the halohydrin is substantially complete, the reaction mixture is acidified to liberate the free acid. In some cases, the product precipitates from the reaction mixture and thus can be isolated by filtration, otherwise the product can be isolated by extraction with a solvent immiscible with water, e.g., ethyl acetate, methylene chloride, diethyl ether and the like, evaporation and crystallization or chromatography.

The 4-[o-, m- or p-(3-amino-2-hydroxypropoxy)-phenyl]-1,2,3-thiadiazole compounds of formula (A) can be prepared by treatment of the 4(o-, m- or p-epoxypropoxy)phenylthiadiazole compounds of formula VII with ammonia or with a primary amine, optionally in the presence of in an inert organic solvent, using particularly a lower aliphatic alcohol as solvent, e.g., methanol, ethanol, isopropanol, t-butanol and the like. The reaction is conducted at a temperature comprised between room temperature and reflux, for about 4 hours to several days, the optimum conditions depending upon the particular starting compound of formula VII and the amine used. Suitable primary amines are the lower alkyl amines such as methylamine, ethylamine, n-propylamine, isopropylamine, n-butylamine, t-butylamine, etc., cyclic amines such as cyclopropylamine, cyclopentylamine, cyclohexylamine, etc., arylamines such as aniline, o- and p-toluidine, and the like, aralkylamines such as benzylamine, phenethylamine, phenylpropylamine, etc., and substituted aralkylamines such as 4-carbamoylphenoxyethylamine.

The preferred amines used are t-butylamine, isopropylamine and 4-carbamoylphenoxyethylamine.

The compounds of formula (A) in which $R^1$ is carboxy or carboalkoxy other than carboethoxy can be alternatively prepared by basic hydrolysis of the corresponding carboethoxy derivatives (A, $R^1$=carboethoxy) using an alkali metal hydroxide in a lower aliphatic alcohol, e.g., methanol or ethanol for 3 to 5 hours, followed by evaporation of the solvent, disolution of the residue in water and filtration of the aqueous solution through a column of a strongly acidic cation exchange resin (in $H^+$ form) such as sold under the trademark Dowex 50, acid form (+), by the Dow Chemical Company, eluting the column first with water and thereafter with dilute acetic acid, e.g., 10% aqueous acetic acid. The acidic eluates are evaporated, and liophylized, to yield the free acids (A, $R^1$=COOH), which are converted into the carbalkoxy derivatives other than carboethoxy by the Fischer's esterification method, i.e., by reaction with a lower aliphatic alochol e.g., methanol, propanol and isopropanol in the presence of hydrogen chloride, at a temperature comprised between room temperature and reflux for a prolonged period of time, of the order of 24 hours to several days followed by base treatment to decompose the hydrochloride salt formed. The carbomethoxy derivative can be alternatively obtained by the method of G. Hallas (J. Chem. Soc. 5770, 1965) using boron trifluoride-methanol as reagent.

Alternatively, the compounds of formula (A) in which $R^1$ is a carboalkoxy group other than carboethoxy can be prepared by selective esterification of the carboxy group in compounds of formula IV by the Fischer's method, or with boron trifluoride-methanol, as previously mentioned, followed by transformation into the epoxypropoxy derivative (VII, $R^1$=carboalkoxy) and treatment of the latter with the desired amine.

The novel thiadiazole derivatives of formula (B) can be prepared by a process illustrated by the following sequence of reactions:

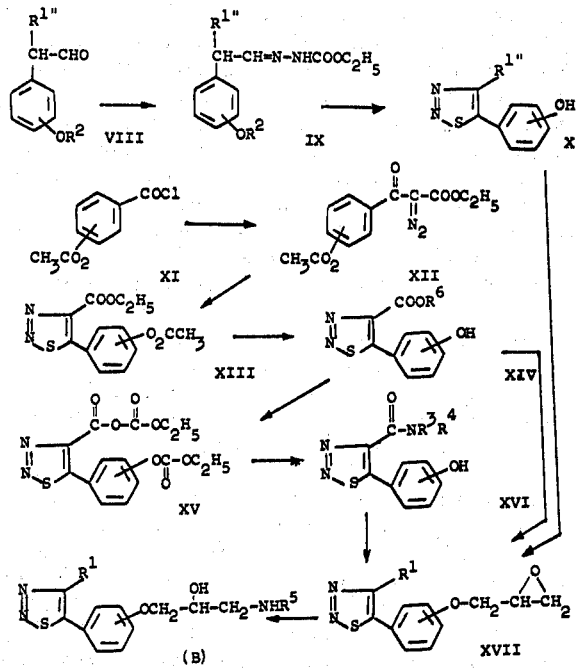

wherein
$R^{1''}$ is hydrogen, lower alkyl, trifluoromethyl, cyano or phenyl;
$R^2$ is hydrogen or tetrahydropyranyl;
$R^6$ is hydrogen or ethyl; and
$R^1$, $R^3$, $R^4$ and $R^5$ are as defined above.

With reference to the above reaction sequences, an ortho-, meta- or para-hydroxy substituted phenylacetaldehyde or the tetrahydropyranyloxy derivative thereof (VIII) is condensed with carbethoxyhydrazine and the hydrazone thus obtained (IX) is cyclized with thionyl chloride to yield the 4-substituted 5-thiadiazole intermediate compounds of formula X, as described hereinbefore in detail with regard to the transformation of the phenyl ketones of formula (I) into the 5-substituted-4-thiadiazole intermediates of formula III. When the starting material is a tetrahydropyranyloxyphenylacetaldehyde (VIII, $R^2$=tetrahydropyranyl) the tetrahydropyranyloxy function is partially hydrolyzed during the hydrazone formation, and completely hydrolyzed during the cyclization. It has been noted that better yields of the thiadiazole compounds (X) are obtained starting from a tetrahydropyranyloxyphenylacetaldehyde.

The 4-carboxy (carboethoxy)-5-hydroxyphenyl substituted and 4-aminocarbonyl-5-hydroxyphenyl substituted thiadiazole intermediates of formulas XIV and XVI, respectively, can be obtained by the following process:

An o, m or p-acetoxybenzoic acid chloride (XI) is treated with an excess of at least 2 molar equivalents of ethyldiazoacetate, to yield the corresponding acetoxybenzoyl diazoacetate of formula XII. This reaction is conducted at a temperature comprised between 0°C to 45°C, for a period of time of the order of 4 to 24 hours. In the preferred embodiments, the compound of formula XI is mixed together with ethyl diazoacetate at low temperature, i.e., at about 0°–5°C, maintaining the reaction mixture at a temperature not higher than room temperature for about 1 to 4 hours, and thereafter under slight heating, i.e., at about 30° to 45°C until the reaction is complete, i.e., for about 4 to 18 hours, until the evolution of gas ceases.

Upon reaction of the diazo compounds of formula XII with hydrogen sulfide in the presence of ammonium polysulfide, in an inert organic solvent or mixture of solvents there are obtained the thiadiazole intermediates of formula XIII. This transformation is preferably effected by dissolving the diazo compound of formula XII in a water miscible inert organic solvent, i.e., a lower aliphatic alcohol such as methanol or ethanol, dioxane or tetrahydrofuran, or mixtures thereof, treating the solution with an aqueous solution of ammonium polysulfide and thereafter bubbling hydrogen sulfide through the mixture, at room temperature for about 5 to 6 hours, 4 hours being generally sufficient. The thiadiazole intermediate of formula XIII precipitates and can be isolated from the mixture by filtration. The acetoxy group can be selectively hydrolyzed by mild alkaline treatment, i.e., by passing a solution of a compound of formula XIII through alkaline alumina, or by treatment with an alkali metal carbonate in methanol, at room temperature, thereby yielding the compounds of formula XIV ($R^6$=Et). The carboethoxy function is then hydrolyzed under more drastic conditions, i.e., by reflux with an alcoholic solution of sodium or potassium hydroxide, for about 2 to 5 hours followed by neutralization with acid to yield the free acid compound (XIV, $R^6$=H). Alternatively, both the acetoxy and carboethoxy functions can be hydrolyzed in a single step, by the latter method.

The transformation of compounds of formula XIV, ($R^6$=H) into the aminocarbonyl-5-hydroxyphenyl thiadiazole compounds for formula XVI is effected via formation of the mixed carboxylic-carbonic anhydride followed by treatment with an amine and optional base treatment, as described above (IV → V → VI).

The compounds of formulas X, XIV ($R^6$=Et) and XVI are then converted into the respective epoxypropoxy derivatives of formula XVII by reaction with epichlorohydrin or epibromohydrin in the presence of an alkali metal hydroxide. Upon reaction of compounds of formula XVII with ammonia or a primary amine there are produced the desired 5-[o, m, or p-(3-amino-2-hydroxypropoxy)phenyl]-1,2,3-thiadiazole compounds of formula (B). The above transformations have been described in detail hereinbefore with regard to the obtention of compounds of formula (A).

The compounds of formula (B) in which $R^1$ is carboxy or carboalkoxy other than carboethoxy can be prepared from the carboethoxy compound (B, $R^1$=carboethoxy) as previously mentioned in connection with the corresponding compounds in the 4-thiadiazole series, represented by formula (A).

The pharmaceutically acceptable acid addition salts of the compounds of formulas (A) and (B) can be conveniently prepared by dissolving the free amino compounds in an alcoholic solvent and adding an excess of an alcoholic solution of an acid such as hydrochloric acid, sulfuric acid, phosphoric acid, citric acid, maleic acid and the like, to precipitate the corresponding salts, which can be separated by filtration and purified by recrystallization.

The starting materials of formulas I, VIII and XI for the obtention of the compounds of the present invention are known compounds or can be prepared from commercially available compounds by known methods. Thus 2,3- and 4-hydroxyacetophenone and 2 and 4-hydroxypropiophenone are commercially available, 3-hydroxypropiophenone has been described by W. H. Wartung et al. in *J. Am. Chem. Soc.* 53, 4149 (1939), 2-hydroxybenzoylacetonitrile has been described by Y. Kawase et al., in *Bull. Chem. Soc. Japan* 35, 1869 (1962) and 4-hydroxybenzoylacetonitrile in U.S.P. 2,392,167, 2- and 4-hydroxyphenylbenzyl ketones can be obtained as described by M. O. Farooq et al., in Ber. 94, 1996 (1961).

In general, the 2- and 4-hydroxyphenones can be prepared from a phenyl ester, by means of the Fries rearrangement, (A. H. Blatt, Organic Reactions I, p. 342 (New York, 1942), while the 3-hydroxyphenones can be prepared from the corresponding unsubstituted phenones via formation of the 3-nitro derivative, reduction of the nitro group to amino, diazotization and decomposition of the diazotate, as described, for example, by L. C. King et al., in *J. Am. Chem. Soc.*, 67, 2089 (1945).

The compounds of formula I in which $R^{1'}$ is carboethoxy can be prepared from the corresponding hydroxyacetophenone, which is converted into the tetrahydropyranyl ether and thereafter with an enamine, which upon acylation with ethylchlorocarbonate followed by acid treatment produces the desired β-keto ester (See Advances in Organic Chemistry, Methods and Results, Vol. 4, page 57); 2,3 and 4-tetrahydropyranyloxyphenyl-acetaldehydes (VIII, $R^{1''}$ =H) can be prepared from the corresponding hydroxyphenylacetic acids via formation of the methyl ester, etherification of the hydroxyl group with dihydropyran, reduction of the carbomethoxy group to the alcohol with lithium aluminum hydride, and oxidation of the alcohol to the aldehyde.

The compounds of formula VIII, ($R^{1''}$ = lower alkyl) can be prepared from the corresponding tetrahydropyranyl ethers of hydroxyphenylacetic acids, which are alkylated in the α-position to the carboxy function via formation of the anion with LiN(iPr)$_2$, treatment of the anion with the desired lower alkyl halide, esterification, reduction of the carboxylate to the alcohol and oxidation to the aldehyde.

The cyano phenylacetaldehyde compounds of formula VIII (R$^{1''}$ =CN) can be obtained from the corresponding tetrahydropyranyloxyphenyl acetonitrile compounds by formation of the anion with LiN(iPr)$_2$, reaction of the anion with ethyl formate and acid treatment.

The trifluoromethylphenylacetaldehyde compounds of formula VIII (R$^{1''}$ =CF$_3$) can be prepared from the corresponding hydroxylated $\alpha,\alpha,\alpha$-trifluoroacetophenones, by protection of the hydroxyl group as the tetrahydropyranyl ether, treatment with methoxymethylenetriphenylphosphorane to form the methoxymethylene derivative, hydrolysis by brief treatment with an acid, such as hydrochloric acid or perchloric acid, [S. G. Levine et al., *J. Am. Chem. Soc.* 80, 6150 (1958)] and optional reetherification of the hydroxyl group.

The compounds of formula VIII in which R$'''$ is phenyl can be prepared from the tetrahydropyranyl ethers of o-, m- or p-hydroxybenzophenones, by the method of E. J. Corey et al. [*J. Am. Chem. Soc.*, 87, 1353 (1965)], which comprises treatment of a keto compound with dimethyloxosulfonium methylide to form an oxirane intermediate, which is decomposed by reaction with boron trifluoride etherate.

The o-, m-, or p-acetoxybenzoic acid chlorides of formula XI are prepared in a conventional manner from the commercially available o-, m- or p-acetoxybenzoic acid.

The compounds of the invention are useful in the treatment and palliation of cardiovascular abnormalities in mammals and primarily achieve their therapeutic action by blocking the cardiac $\beta$-adrenergic receptor sites. The compounds are especially useful in the treatment or palliation of cardiac arrhythmias, angina pectoris, hypertrophic subaortic stenosis, pheochromocytoma, thyrotoxicosis, hyperkinetic syndromes, tetralogy of Fallot, mitral stenosis with tachycardia, general ischemic conditions, and hypertension founded on elevated cardiac outputs due to a hyperadrenergic state. The compounds are active both in the treatment or palliation of acute attacks of such cardiac disorders, and further can be applied prophylactically to prevent or reduce the frequency of such attacks. This prophylactic action is particularly desirable in reducing the frequency of attacks of angina pectoris, since the medication (i.e., nitroglycerin) presently commonly used in the treatment of angina pectoris has no recognized prophylactic action. The cardiac selective compounds (e.g., 4-[4{3(4-carbamoylphenoxyethylamino)-2-hydroxypropoxy}phenyl]-1,2,3-thiadiazole) are especially useful as they can also be applied to treat cardiac abnormalities in patients suffering from asthma or chronic obstructive lung disease.

Additional information concerning the use, action and determination of $\beta$-blockers can be obtained by reference to the literature such as, for example, Dotlery et al., *Clinical Pharmacology and Therapeutics*, volume 10, No. 6, 765–797 and the references cited therein.

The compounds of the invention can be administered in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the pharmaceutically acceptable salts of the compounds of formula I and a pharmaceutical carrier. The pharmaceutical carrier can be either a solid material or liquid, in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs and optionally can contain small quantities of preservatives and/or buffering agents.

The solid compositions can take the form of tablets, powders, capsules, pills or the like, preferable in unit dosage forms for simple administration or precise dosages. Suitable solid carriers include, for example, pharmaceutical grades of starch, lactose, sodium saccharin, sodium bisulfite and the like.

The compounds of this invention are typically administered in dosages of about from 0.01 to 5 mg. per Kg. of body weight. The precise effective dosage will, of course, vary depending upon the mode of administration, the condition being treated and the host. Preferably, the compounds are administered orally, either as solid compositions, e.g., tablets or liquids as described herein above.

The following Preparations and Examples illustrate the invention but are not intended to limit its scope.

PREPARATION 1

To 150 ml. of sulfuric acid, cooled to −10°C are added dropwise, in a 15 minute period and under stirring, 60 g. of $\beta,\beta,\beta$-trifluoropropiophenone, maintaining the temperature of the reaction mixture at about −5°C. The reaction mixture is stirred at 0°C for 90 minutes and then treated dropwise with a cooled nitrating mixture prepared from 40 ml. of nitric acid and 60 ml. of sulfuric acid, maintaining the temperature of the reaction mixture at about 0°C. The resulting mixture is stirred for 30 minutes further at about 0°C, and poured into ice water. The formed precipitate is collected by filtration and dried, thus obtaining 3-nitro-$\beta,\beta,\beta$-trifluoropropiophenone.

To a mixture of 120 g. of stannous chloride dihydrate and 106 ml. of concentrated hydrochloric acid cooled to 0°C is added 25 g. of 3-nitro-$\beta,\beta,\beta$-trifluoropropiophenone. The reaction mixture is maintained at a temperature not higher than 35°C for 2 hours. It is then refluxed for 10 minutes, cooled and the formed precipitate filtered off. The solid material is then treated with 350 ml. of 30% sodium hydroxide and the mixture stirred for 30 minutes at 0°C. The solid material is separated by filtration and crystallized from ethanol-water, to yield 3-amino-$\beta,\beta,\beta$-trifluoropropiophenone.

To a mixture of 150 ml. of water and 112 ml. of sulfuric acid cooled to 0°C is added 13.5 g. of 3-amino-$\beta,\beta,\beta$-trifluoropropiophenone and the reaction mixture is stirred for 30 minutes. The resulting solution is treated dropwise with a solution of 8.2 g. of sodium nitrite in 20 ml. of water, at 0°C. The reaction mixture is allowed to stand at room temperature for 2 hours, it is then made alkaline by the addition of 30% sodium hydroxide solution and extracted with ethyl acetate to eliminate undesired products. The aqueous phase is acidified with 10% hydrochloric acid solution and extracted with ethyl acetate. The latter ethyl acetate extracts are washed with water, dried over sodium sulfate and evaporated to a small volume, until crystallization starts. The formed precipitate is collected by filtration and dried thus obtaining 3-hydroxy-β,β,β-trifluoropropiophenone (3-hydroxy-α-trifluoromethyl acetophenone).

In a similar manner, starting from α,α,α-trifluoroacetophenone, propiophenone, butyrophenone, valerophenone, benzoylacetonitrile and phenyl benzyl ketone there are respectively obtained: 3-hydroxy-α,α,α-trifluoroacetophenone, 3-hydroxypropiophenone, 3-hydroxybutyrophenone, 3-hydroxyvalerophenone, 3-hydroxybenzoylacetonitrile, and 3-hydroxyphenyl benzyl ketone.

PREPARATION 2

A. To a mixture of 94 g. of phenol and 88 g. of n-butyric acid is added, in a 30 minute period, 122.8 g. of freshly distilled thionyl chloride. The reaction mixture is heated to 40°C until the evolution of sulfur dioxide and hydrochloric acid ceases and then distilled under high vacuo, to obtain the pure phenyl butyrate.

B. To a stirred mixture of 146.3 g. of anhydrous aluminum chloride and 400 ml. of carbon disulfide is added dropwise, in a 2 hour period, 164 g. of phenyl butyrate. Hydrogen chloride evolves spontaneously. When the addition is complete the reaction mixture is heated to reflux for about 2 hours, until the evolution of hydrogen chloride ceases. The carbon disulfide is eliminated by distillation and the residue is heated in an oil bath at 140° to 150°C, under stirring. The reaction mixture is cooled, the aluminum complex is decomposed by careful addition of 150 ml. of concentrated hydrochloric acid and 500 ml. of water, and the mixture is maintained at 0°C for 18 hours. The solid is separated by filtration and recrystallized from methanol, thus obtaining 4-hydroxybutyrophenone. The filtrate is treated with 10% sodium hydroxide solution and extracted with ether to remove non-phenolic products. The alkaline solution is acidified with hydrochloric acid and the oily layer is separated, dried over magnesium sulfate and distilled, thus obtaining 2-hydroxybutyrophenone and an additional amount of 4-hydroxybutyrophenone.

In a similar manner but using n-valeric acid in place of n-butyric acid in part A, there are obtained 4-hydroxyvalerophenone and 2-hydroxyvalerophenone.

PREPARATION 3

A. A mixture of 37 g. of 4-hydroxyphenylacetic acid, 370 ml. of methanol and 0.1 ml. of sulfuric acid is refluxed for 6 hours, cooled, poured into ice water, and extracted with methylene chloride. The organic extract is washed with water to neutrality, dried over sodium sulfate and evaporated to dryness under vacuo, to yield methyl 4-hydroxyphenylacetate.

B. A mixture of 38.5 g. of methyl 4-hydroxyphenylacetate, 3.8 l. of benzene and 0.9 g. of p-toluenesulfonic acid is heated to the boiling point and about 20 ml. of solvent are distilled to remove moisture, it is then cooled to room temperature and treated with 130 ml. of freshly distilled dihydropyran. The reaction mixture is kept at room temperature for 1 hour and washed with 10% sodium bicarbonate solution and water, dried over sodium sulfate and evaporated to dryness under reduced pressure. The residue is dissolved in methylene chloride and filtered through neutral alumina, thus obtaining the pure methyl 4-(tetrahydropyran-2-yloxy)phenylacetate.

C. A solution of 57 g. of methyl 4-(tetrahydropyran-2-yloxy)phenylacetate, in 2 l. of anhydrous tetrahydrofuran is added dropwise, over a 30 minute period to a stirred suspension of 20 g. of lithium aluminum hydride in 1 l. of anhydrous tetrahydrofuran, under nitrogen atmosphere. The mixture is refluxed for 90 minutes, cooled and cautiously treated with 20 ml. of ethyl acetate, to destroy the excess reagent. Solid sodium sulfate is added, the inorganic material filtered off and thoroughly washed with hot ethyl acetate. Upon evaporation of the combined organic filtrates there is obtained 4-(tetrahydropyran-2-yloxy)phenylethanol.

D. To a stirred suspension of 740 g. of Celite diatomaceous earth and 396 g. of chromium trioxide-dipyridine complex (Collins' reagent) in 4 l. of anhydrous methylene chloride, cooled to 0°C is added dropwise a solution of 58 g. of 4-(tetrahydropyran-2-yloxy)-phenylethanol in 3 l. of anhydrous methylene chloride, maintaining the temperature of the reaction mixture at 0°–5°C. After completion of the addition, the reaction mixture is stirred for 30 minutes further at 0°C, 396 g. of sodium bisulfate are added and the mixture stirred for 15 additional minutes. It is then filtered through anhydrous magnesium sulfate and evaporated to dryness under reduced pressure, to yield 4-(tetrahydropyran-2-yloxy)phenylacetaldehyde.

By repeating the above-mentioned procedures, using 2-hydroxyphenylacetic acid and 3-hydroxyphenylacetic acid as starting materials in part A, there are obtained as final products 2-(tetrahydropyran-2-yloxy)phenylacetaldehyde and 3-(tetrahydropyran-2-yloxy)phenylacetaldehyde, respectively.

PREPARATION 4

By following the method of Preparation 3 part B, 4-hydroxyacetophenone is converted into its tetrahydropyranylether.

To a stirred solution of 10 g. of 4-tetrahydropyran-2-yloxyacetophenone in 250 ml. of benzene, thiophene free are added 10 ml. of pyrrolidine and 100 mg. of p-toluenesulfonic acid and the resulting mixture is refluxed for 2 hours, with continuous distillation of the water formed during the reaction using a Dean Stark trap. The solvent and excess pyrrolidine are then removed under vacuo. The crude pyrrolidine enamine thus obtained is dissolved in 200 ml. of benzene, 4.1 g. of ethyl chlorocarbonate are added and the resulting mixture is refluxed for 10 hours, cooled and treated with 10 ml. of 10% hydrochloric acid. The reaction mixture is stirred for 20 hours at room temperature, and diluted with water. The organic phase is separated and the aqueous phase extracted with ethyl acetate. The combined organic solutions are washed with 10% sodium carbonate solution and water to neutrality, dried over sodium sulfate and evaporated to dryness under reduced pressure. The residue is purified by crystallization to yield ethyl 3-keto-4-hydroxyphenylpropionate.

In a similar manner starting from 2-hydroxyacetophenone and 4-hydroxyacetophenone there are obtained as final products ethyl 3-keto-2-hydroxyphenylpropionate and ethyl 3-keto-4hydroxyphenylpropionate, respectively.

PREPARATION 5

To a solution of 20.2 g. of diisopropylamine in 200 ml. of anhydrous tetrahydrofuran cooled to 0°C is added 12.8 g. of n-butyllithium, under nitrogen atmosphere and under stirring. To the resulting mixture is added dropwise a solution of 20.6 g. of 4-(tetrahydropyran-2-yloxy)phenylacetic acid (prepared from the corresponding methyl ester by selective hydrolysis of the carbomethoxy group with base followed by careful neutralization with acetic acid) in 250 ml. of anhydrous tetrahydrofuran, maintaining the temperature at 0°–5°C. The reaction mixture is stirred at 0°C for 30 minutes, 36.5 g. of methyl bromide is added and the resulting mixture is stirred for 16 hours at room temperature, under nitrogen atmosphere. It is then poured into 5% sodium carbonate solution, and extracted with methylene chloride. The aqueous phase is acidified with 4N hydrochloric acid, extracted with ether and the organic extract washed with water, dried over sodium sulfate and evaporated to dryness under vacuo. The crude residue is esterified with methanol-sulfuric acid and thereafter treated with dihydropyran, in accordance with the methods or Preparation 3 parts A and B, to yield methyl 2-methyl-2-(4-tetrahydropyran-2-yloxyphenyl) acetate.

In a similar manner but using equimolecular amounts of ethyl bromide, n-propyl bromide, isopropyl bromide and n-butyl bromide in place of methyl bromide there are respectively obtained:

methyl 2-ethyl-2-(4-tetrahydropyran-2-yloxyphenyl) acetate, methyl 2-propyl-2-(4-tetrahydropyran-2-yloxyphenyl) acetate, methyl 2-isopropyl-2-(4-tetrahydropyran-2-yloxyphenyl) acetate, and methyl 2-butyl-2(4-tetrahydropyran-2-yloxyphenyl) acetate.

By the same method but using 2-(tetrahydropyran-2-yloxy) phenylacetic acid and 3-(tetrahydropyran-2-yloxy)-phenylacetic acid in place of 4-(tetrahydropyran-2-yloxy)-phenylacetic acid and methyl bromide as alkylating agent there are obtained methyl 2-methyl-2-(2-tetrahydropyran-2-yloxyphenyl)acetate and methyl 2-methyl-2-(3-tetrahydropyran-2-yloxyphenyl)acetate, respectively.

PREPARATION 6

By following the methods of Preparation 3, parts C and D, methyl 2-methyl-2-(4-tetrahydropyran-2-yloxyphenyl)acetate is converted successively into 2-methyl-2-(4-tetrahydropyran-2-yloxyphenyl)ethanol and 2-methyl-2-(4-tetrahydropyran-2-yloxyphenyl-)acetaldehyde.

In a similar manner from the remaining compounds obtained in Preparation 5 there are produced as final products respectively:

2-ethyl-2-(4-tetrahydropyran-2-yloxyphenyl) acetaldehyde, 2-propyl-2-(4-tetrahydropyran-2-yloxyphenyl-)acetaldehyde, 2-isopropyl-2-(4-tetrahydropyran-2-yloxyphenyl-)acetaldehyde, 2-butyl-2-(4-tetrahydropyran-2-yloxyphenyl-)acetaldehyde, 2-methyl-2-(2-tetrahydropyran-2-yloxyphenyl-)acetaldehyde and 2-methyl-2-(3-tetrahydropyran-2-yloxyphenyl-)acetaldehyde.

PREPARATION 7

By following the method of Preparation 3, part B, 10 g. of 4-hydroxyphenylacetonitrile are converted into (4-tetrahydropyran-2-yloxy)phenylacetonitrile.

To a cold (0°C) solution of 20.2 g. of diisopropylamine in 70 ml. of anhydrous tetrahydrofuran, is added 12.8 g. of n-butyllithium, and 10 g. of 4-tetrahydropyran-2-yloxyphenylacetonitrile, under nitrogen atmosphere, the resulting mixture is stirred at 0°C for 30 minutes and then 7.4 g. of ethyl formate is added. The reaction mixture is stirred for 18 hours at room temperature, under nitrogen atmosphere, poured into ice water and acidified to pH 5 with 10% acetic acid. It is then extracted three times with methylene chloride, the organic extracts are washed with water to neutrality, dried over sodium sulfate and evaporated to dryness under vacuo. The crude residue is treated with dihydropyran in benzene solution, in accordance with the method of Preparation 3, part B, to afford 2-cyano-2-(4-tetrahydropyran-2-yloxyphenyl)acetaldehyde which can be purified by crystallization from acetone-hexane.

In a similar manner 2-hydroxyphenylacetonitrile and 3-hydroxyphenylacetonitrile are converted respectively into 2-cyano-2-(2-tetrahydropyran-2-yloxyphenyl)acetaldehyde and 2-cyano-2-(3-tetrahydropyran-2-yloxyphenyl)acetaldehyde.

PREPARATION 8

To an ethereal solution of 0.2 molar equivalents of methoxymethylenetriphenylphosphorane, prepared as described by S. G. Levine in *J. Am. Chem. Soc.*, 80, 6150 (1958) is added a soluiton of 0.1 molar equivalents of 2-(tetrahydropyran-2-yloxy)-α,α,α-trifluoroacetophenone (prepared by conventional etherification of 2-hydroxy-α,α,α-trifluoroacetophenone [S. Matsumoto et al., *Bull. Soc. Chim. Japan* 42, 960 (1969)] with dihydropyran, as described in Preparation 3 part B) in 100 ml. of anhydrous ether in a dropwise fashion, under nitrogen atmosphere. The reaction mixture is allowed to stand at room temperature for 2 hours. It is then diluted with 10% acetic acid, the organic phase separated and the aqueous phase extracted with ether. The combined organic extracts are washed with water, dried and evaporated to dryness. The residue is dissolved in diethyl ether previously saturated with 72% perchloric acid, and the resulting solution is stirred at room temperature for 30 minutes. It is then washed with sodium carbonate solution and water, dried over sodium sulfate and evaporated to dryness under vacuo. The crude residue is treated with dihydropyran in the presence of p-toluenesulfonic acid, in accordance with the method of Preparation 3 part B, thus obtaining 2-trifluoromethyl-2-(2-tetrahydropyran-2-yloxyphenyl)acetaldehyde.

In a similar manner, 3-(tetrahydropyran-2-yloxy)-α,α,α-trifluoroacetophenone and 4-(tetrahydropyran-2-yloxy)-α,α,α-trifluoroacetophenone are converted respectively into 2-trifluoromethyl-2-(3-tetrahydropyran-2-yloxyphenyl)acetaldehyde and 2-trifluoromethyl-2-(4-tetrahydropyran-2-yloxyphenyl)acetaldehyde.

PREPARATION 9

By following the method of Preparation 3 part B, 4-hydroxybenzophenone is converted into the tetrahydropyranylether.

To 0.013 molar equivalents of dimethyloxosulfonium metilide reagent, prepared from 0.013 mole of sodium hydride, 0.013 mol of trimethyloxosulfonium iodide and 15 ml. of anhydrous dimethylsulfoxide, as described by E. J. Corey et al., in *J. Am. Chem. Soc.*, 87,1353 (1965) is added 0.01 molar equivalents (2.8 g.) of 4-(tetrahydropyran-2-yloxy)benzophenone in 10 ml. of anhydrous dimethylsulfoxide at room temperature and under nitrogen atmosphere. The reaction mixture is heated to 50°C for 1 hour under anhydrous conditions, cooled, diluted with water and extracted with ethyl acetate. The combined organic extracts are washed with water, dried over sodium sulfate and evaporated to dryness under vacuo. The residue is purified by thin layer chromatography, thus obtaining 1-(4-tetrahydropyran-2-yloxyphenyl)-1-phenyl-oxirane.

To a stirred solution of 1 g. of the foregoing compound in 25 ml. of anhydrous ether, cooled to 0°C is added 0.5 ml. of boron trifluoride etherate. The resulting mixture is stirred at room temperature for 15 minutes, diluted with ether and washed with sodium bicarbonate solution and water to neutrality, dried over sodium sulfate and evaporated to dryness under vacuo. Purification of the residue by thin layer chromatography affords the pure 2-phenyl-2-(4tetrahydropyran-2-yloxyphenyl)acetaldehyde.

In a similar manner, starting from 2-hydroxybenzophenone and 3-hydroxybenzophenone there are obtained as final products 2-phenyl-2-(2-tetrahydropyran-2-yloxyphenyl) acetaldehyde and 2-phenyl-2-(3-tetrahydropyran-2-yloxyphenyl) acetaldehyde, respectively.

EXAMPLE 1

To a solution of 13.61 g. of 4-hydroxyacetophenone in 250 ml. of methanol is added a solution of 15.8 g. of carbethoxyhydrazine in 250 ml. of methanol and 50 ml. of glacial acetic acid, and the reaction mixture is refluxed for 4 hours. It is then evaporated to dryness under reduced pressure and the solid residue recrystalized from methanol-water, to yield the ethoxycarbonylhydrazone of 4-hydroxyacetophenone.

EXAMPLE 2

To a solution of 1 g. of 2-hydroxyacetophenone in 25 ml. of methanol is added a solution of 1.895 g. of carbethoxyhydrazine in 25 ml. of methanol and 0.5 ml. of glacial acetic acid. The reaction mixture is refluxed for 17 hours, cooled and poured into water, and the formed precipitate collected by filtration, dried and purified by crystallization from methanol-water, thus obtaining the pure ethoxycarbonylhydrazone of 2-hydroxyacetophenone.

By following the method of this Example or the method of Example 1,
  3-hydroxyacetophenone,
  2-hydroxypropiophenone,
  3-hydroxypropiophenone,
  4-hydroxypropiophenone,
  2-hydroxybutyrophenone,
  3-hydroxybutyrophenone,
  2-hydroxyvalerophenone,
  3-hydroxyvalerophenone,
  4-hydroxyvalerophenone,
  2-hydroxybenzoylacetonitrile,
  3-hydroxybenzoylacetonitrile,
  4-hydroxybenzoylacetonitrile,
  2-hydroxy-α-trifluoromethylacetophenone,
  3-hydroxy-α-trifluoromethylacetophenone,
  2-hydroxyphenyl benzyl ketone,
  4-hydroxyphenyl benzyl ketone,
  3-hydroxyphenyl benzyl ketone,
  ethyl 3-keto-2-hydroxyphenylproprionate,
  ethyl 3-keto-3-hydroxyphenylpropionate and
  ethyl 3-keto-4-hydroxyphenylpropionate,
are converted into the corresponding ethoxycarbonylhydrazones.

EXAMPLE 3

To 2.5 ml. of freshly distilled thionyl chloride, cooled to 0° C is added portionwise, 1.12 g. of the ethoxycarbonylhydrazone of 4-hydroxyacetophenone, maintaining the reaction mixture at room temperature or below until the evolution of gas ceases. It is then heated to reflux under anhydrous conditions for 1 hour. At the end of this time the excess thionyl chloride is eliminated under reduced pressure, the yellowish crystalline residue is treated three times with toluene and evaporated to dryness to completely eliminate the thionyl chloride and thereafter crystallized from methanolwater, thus affording the pure 4-(4-hydroxyphenyl)-1,2,3-thiadiazole.

In a similar manner, starting from the ethoxycarbonylhydrazones obtained in Example 2 there are produced:
  4-(2-hydroxyphenyl)-1,2,3-thiadiazole,
  4-(3-hydroxyphenyl)-1,2,3-thiadiazole,
  4-(2-hydroxyphenyl)-5-methyl-1,2,3-thiadiazole,
  4-(3-hydroxyphenyl)-5-methyl-1,2,3-thiadiazole,
  4-(4-hydroxyphenyl)-5-methyl-1,2,3-thiadiazole,
  4-(2-hydroxyphenyl)-5-ethyl-1,2,3-thiadiazole,
  4-(3-hydroxyphenyl)-5-ethyl-1,2,3-thiadiazole,
  4-(2-hydroxyphenyl)-5-propyl-1,2,3-thiadiazole,
  4-(3-hydroxyphenyl)-5-propyl-1,2,3-thiadiazole,
  4-(4-hydroxyphenyl)-5-propyl-1,2,3-thiadiazole,
  4-(2-hydroxyphenyl)-5-cyano-1,2,3-thiadiazole,
  4-(3-hydroxyphenyl)-5-cyano-1,2,3-thiadiazole,
  4-(4-hydroxyphenyl)-5-cyano-1,2,3-thiadiazole,
  4-(2-hydroxyphenyl)-5-trifluoromethyl-1,2,3-thiadiazole,
  4-(3-hydroxyphenyl)-5-trifluoromethyl-1,2,3-thiadiazole,
  4-(4-hydroxyphenyl)-5-trifluoromethyl-1,2,3-thiadiazole,
  4-(2-hydroxyphenyl)-5-phenyl-1,2,3-thiadiazole,
  4-(4-hydroxyphenyl)-5-phenyl-1,2,3-thiadiazole,
  4-(3-hydroxyphenyl)-5-phenyl-1,2,3-thiadiazole,
  4-(2-hydroxyphenyl)-5-carboethoxy-1,2,3-thiadiazole,
  4-(3-hydroxyphenyl)-5-carboethoxy-1,2,3-thiadiazole and
  4-(4-hydroxyphenyl)-5-carboethoxy-1,2,3-thiadiazole.

EXAMPLE 4

To a solution of 0.112 g. of sodium hydroxide in 10 ml. of water is added 0.499 g. of 4-(4-hydroxyphenyl)1,2,3-thiadiazole and to the resulting solution is added dropwise, under stirring, 0.66 ml. of epibromohydrin, in a 5 minute period. The reaction mixture is stirred for 48 hours and extracted several times with ethyl acetate. The combined organic extracts are washed with water to neutrality, dried over anhydrous sodium sulfate and evaporated to dryness under vacuo. The semisolid residue is crystallized from methylene chloride-hexane to yield the pure 4-[4(2,3-epoxypropoxy)phenyl] 1,2,3-thiadiazole.

In a similar manner, the remaining compounds obtained in Example 3 are converted respectively into:
  4-[2(2,3-epoxypropoxy)phenyl] -1,2,3-thiadiazole,
  4-[3(2,3-epoxypropoxy)phenyl]-1,2,3-thiadiazole,
  4-[2(2,3-epoxypropoxy)phenyl]-5-methyl-1,2,3-thiadiazole,
  4-[3(2,3-epoxypropoxy)phenyl]-5-methyl-1,2,3-thiadiazole,
  4-[4(2,3-epoxypropoxy)phenyl]-5-methyl-1,2,3-thiadiazole,
  4-[2(2,3-epoxypropoxy)phenyl]-5-ethyl-1,2,3-thiadiazole,
  4-[3(2,3-epoxypropoxy)phenyl]-5-ethyl-1,2,3-thiadiazole, 4-[2(2,3-epoxypropoxy)phenyl]-5-propyl-1,2,3-thiadiazole,
4-[3(2,3-epoxypropoxy)phenyl]-5-propyl-1,2,3-thiadiazole,
4-[4(2,3-epoxypropoxy)phenyl]-5-propyl-1,2,3-thiadiazole,
4-[2(2,3-epoxypropoxy)phenyl]-5-cyano-1,2,3-thiadiazole,
4-[3(2,3-epoxypropoxy)phenyl]-5-cyano-1,2,3-thiadiazole,
4-[4(2,3-epoxypropoxy)phenyl]-5-cyano-1,2,3-thiadiazole,
4-[2(2,3-epoxypropoxy)phenyl]-5-trifluoromethyl-1,2,3-tiadiazole,
4-[3(2,3-epoxypropoxy)phenyl]-5-trifluoromethyl-1,2,3-thiadiazole,
4-[4(2,3-epoxypropoxy)phenyl]-5-trifluoromethyl-1,2,3-thiadiazole,
4-[2(2,3-epoxypropoxy)phenyl]-5-phenyl-1,2,3-thiadiazole,
4-[4(2,3-epoxypropoxy)phenyl]-5-phenyl-1,2,3-thiadiazole,
4-[3(2,3-epoxypropoxy)phenyl]-5-phenyl-1,2,3-thiadiazole,
4-[2(2,3-epoxypropoxy)phenyl]-5-carboethoxy-1,2,3-thiadiazole,
4-[3(2,3-epoxypropoxy)phenyl]-5-carboethoxy-1,2,3-thiadiazole and
4-[4(2,3-epoxypropoxy)phenyl]-5-carboethoxy-1,2,3-thiadiazole.

EXAMPLE 5

A. To a solution of 660 mg. of 4-[4(2,3-epoxypropoxy)phenyl]-1,2,3-thiadiazole in 29.7 ml. of t-butylamine is added 3.3 ml. of t-butanol and the reaction mixture is stirred at room temperature for 24 hours. It is then evaporated to dryness under vacuo and the residue taken up in methylene chloride. The resulting solution is extracted with dilute hydrochloric acid and the aqueous phase made alkaline with sodium carbonate. It is then extracted with ethyl acetate and the organic extracts washed to neutrality, dried over sodium sulfate and evaporated to dryness. The solid residue is purified by two recrystallizations from methylene chloridehexane (after decolorization with charcoal) and then by three crystallizations from benzene, thus obtaining the pure 4-[4(3-t-butylamino-2-hydroxypropoxy)phenyl]-1,2,3-thiadiazole, m.p. 124°–125°C; λmax 256, 304 nm, (ε 20,000;2,000) ir 3340, 1615, 1580, 1535, 835 cm$^{-1}$.

B. To a solution of 1.95 g. of 4-[2(2,3-epoxypropoxy)phenyl]-1,2,3-thiadiazole in 45 ml. of t-butylamine is added 5 ml. of t-butanol, and the reaction mixture is stirred at room temperature for 5 days. It is then evaporated to dryness under vacuo. Crystallization of the residue from methylene chloride-benzene affords the pure 4-[2(3-t-butylamino-2-hydroxypropoxy)phenyl]1,2,3-thiadiazole, m.p. 99°–100°C λmax 244, 290 nm (ε 10,500, 4,600) ir 3355, 1600 cm$^{-1}$.

In a similar manner, by the methods of parts A or B of this Example, the remaining compounds obtained in Example 5 are converted respectively into:

4-[3-(3-t-butylamino-2-hydroxypropoxy)phenyl]-1,2,3thiadiazole, m.p. 121°–122°C; λmax 211, 243, 290 nm (ε 28,700, 13,800, 3,390); ir 3290, 1605 cm$^{-1}$,
4-[2(3-t-butylamino-2-hydroxypropoxy)phenyl]-5-methyl-1,2,3-thiadiazole,
4-[3(3-t-butylamino-2-hydroxypropoxy)phenyl]-5-methyl-1,2,3-thiadiazole,
4-[4(3-t-butylamino-2-hydroxypropoxy)phenyl]-5-methyl-1,2,3-thiadiazole,
4-[2(3-t-butylamino-2-hydroxypropoxy)phenyl]-5-ethyl-1,2,3-thiadiazole,
4-[3(3-t-butylamino-2-hydroxypropoxy)phenyl]-5-ethyl-1,2,3-thiadiazole,
4-[2(3-t-butylamino-2-hydroxypropoxy)phenyl]-5-propyl-1,2,3-thiadiazole,
4-[3(3-t-butylamino-2-hydroxypropoxy)phenyl]-5-propyl-1,2,3-thiadiazole,
4-[4(3-t-butylamino-2-hydroxypropoxy)phenyl]-5-propyl-1,2,3-thiadiazole,
4-[2(3-t-butylamino-2-hydroxypropoxy)phenyl]-5-cyano-1,2,3-thiadiazole,
4-[3(3-t-butylamino-2-hydroxypropoxy)phenyl]-5-cyano-1,2,3-thiadiazole,
4-[4(3-t-butylamino-2-hydroxypropoxy)phenyl]-5-cyano-1,2,3-thiadiazole,
4-[2(3-t-butylamino-2-hydroxypropoxy)phenyl]-5-trifluoromethyl-1,2,3-thiadiazole,
4-[3(3-t-butylamino-2-hydroxypropoxy)phenyl]-5-trifluoromethyl-1,2,3-thiadiazole,
4-[4(3-t-butylamino-2-hydroxypropoxy)phenyl]-5-trifluoromethyl-1,2,3-thiadiazole,
4-[2(3-t-butylamino-2-hydroxypropoxy)phenyl]-5-phenyl-1,2,3-thiadiazole,
4-[4(3-t-butylamino-2-hydroxypropoxy)phenyl]-5-phenyl-1,2,3-thiadiazole,
4-[2(3-t-butylamino-2-hydroxypropoxy)phenyl]-5-carboethoxy-1,2,3-thiadiazole,
4-[3(3-t-butylamino-2-hydroxypropoxy)phenyl]-5-carboethoxy-1,2,3-thiadiazole, and
4-[4(3-t-butylamino-2-hydroxypropoxy)phenyl]-5-carboethoxy-1,2,3-thiadiazole.

EXAMPLE 6

A. Preparation of carbamoylphenoxyethylamine.

A mixture of 100 g. of methyl p-hydroxybenzoate, 200 g. of anhydrous potassium carbonate, 400 g. of dibromoethane and 1500 ml. of methyl ethyl ketone is refluxed under vigorous stirring for 24 hours, at the end of which time the reaction is essentially complete, as demonstrated by t.l.c. using an ethyl acetate-hexane mixture (60:20) as gradient. The solid is separated by filtration, and the filtrate is evaporated to dryness under vacuo. The oily residue is dissolved in ethyl acetate, washed twice with water, dried over magnesium sulfate and evaporated to dryness under vacuo, to yield methyl 4-(2-bromoethoxy)benzoate.

A mixture of 150 g. of methyl 4-(2-bromoethoxy) benzoate, 80 g. of sodium azide, 1400 ml. of methanol and 300 ml. of water is stirred at 70°C for 16 hours, cooled and concentrated to ⅓ the original volume under reduced pressure, 2 liters of ethyl acetate are added, the organic phase is separated, washed with water, dried over magnesium sulfate and evaporated to a small volume; 1.5 l. of ethanol is added and the volume reduced to approximately 750 ml. The insoluble material is separated by filtration and the filtrate is hydrogenated in the presence of 2 g. of platinum charcoal catalyst, for about 8 hours at room temperature. The catalyst is separated by filtration and the filtrate evaporated to dryness under reduced pressure, to yield methyl 4-(2-aminoethoxy) benzoate.

A mixture of 120 g. of methyl 4-(2-aminoethoxy)benzoate and 1 l. of concentrated ammonium hydroxide is stirred at room temperature for 72 hours. The formed precipitate is separated by filtration and the recrystallized from ethanol, to afford the pure 4-carbamoylphenoxyethylamine.

B. A mixture of 234 mg. of 4-[4(2,3-epoxypropoxy)phenyl]-1,2,3-thiadiazole, 180 mg. of 4-carbamoylphenoxyethylamine and 5 ml. of ethanol is stirred at room temperature for 68 hours. The formed precipitate is collected by filtration and recrystallized from methanol thus obtaining the pure 4-[4{3-(4-carbamoylphenoxyethylamino)2-hydroxypropoxy}phenyl]-1,2,3-thiadiazole, m.p. 173°–174°C; λmax 255 nm (ε 32,300); ir 3,345, 1605, 1570 cm$^{-1}$.

In a similar manner, starting from the corresponding epoxypropoxyphenyl thiadiazole compounds of Example 4, there are produced:
  4-[2{3-(4-carbamoylphenoxyethylamino)-2-hydroxypropoxy}phenyl]-1,2,3,-thiadiazole,
  4-[3{3-(4-carbamoylphenoxyethylamino)-2-hydroxypropoxy}phenyl]-1,2,3-thiadiazole,
  4-[2{3-(4-carbamoylphenoxyethylamino)-2-hydroxypropoxy}phenyl]-1,2,3-thiadiazole,
  4-[3{3-(4-carbamoylphenoxyethylamino)-2-hydroxypropoxy}phenyl]-5-methyl-1,2,3-thiadiazole,
  4-[4{3-(4-carbamoylphenoxyethylamino)-2-hydroxypropoxy}phenyl]-5-methyl-1,2,3-thiadiazole,
  4-[3{3-(4-carbamoylphenoxyethylamino)-2-hydroxypropoxy}phenyl]-ethyl-5-ethyl-1,2,3-thiadiazole,
  4-[2{3-(4-carbamoylphenoxyethylamino)-2-hydroxypropoxy} phenyl]-5-propyl-1,2,3-thiadiazole,
  4-[2{3-(4-carbamoylphenoxyethylamino)-2-hydroxypropoxy}phenyl]-5-cyano-1,2,3-thiadiazole,
  4-[2{3-(4-carbamoylphenoxyethylamino)-2-hydroxypropoxy}phenyl]-5-phenyl-1,2,3-thiadiazole,
  4-[2{3-(4-carbamoylphenoxyethylamino)-2-hydroxypropoxy}phenyl]-5-trifluoromethyl-1,2,3-thiadiazole,
  4-[4{3-(4-carbamoylphenoxyethylamino)-2-hydroxypropoxy}phenyl]-5-phenyl-1,2,3-thiadiazole,
  4-[2{3-(4-carbamoylphenoxyethylamino)-2-hydroxypropoxy}phenyl]-5-carboethoxy-1,2,3-thiadiazole and
  4-[4{3-(4-carbamoylphenoxyethylamino)-2-hydroxypropoxy}phenyl]-5-carboethoxy-1,2,3-thiadiazole.

EXAMPLE 7

A solution of 200 mg. of 4-[4(2,3-epoxypropoxy)phenyl]-1,2,3-thiadiazole in 10 ml. of anhydrous ethanol is saturated with ammonia and the reaction mixture is maintained at room temperature for 16 hours. The reaction mixture is then evaporated to dryness under vacuo, to yield the crude 4-[4(3-amino-2-hydroxypropoxy)phenyl]-1,2,3-thiadiazole, which can be further purified by thin layer chromatography.

In a similar manner from the corresponding epoxypropoxyphenyl thiadiazole compounds prepared in Example 4 there are obtained:
  4-[2(3-amino-2-hydroxypropoxy)phenyl]-1,2,3-thiadiazole,
  4-[3(3-amino-2-hydroxypropoxy)phenyl]-5-methyl-1,2,3-thiadiazole,
  4-[2(3-amino-2-hydroxypropoxy)phenyl]-5-ethyl-1,2,3-thiadiazole,
  4-[4(3-amino-2-hydroxypropoxy)phenyl]-5-cyano-1,2,3-thiadiazole,
  4-[2(3-amino-2-hydroxypropoxy)phenyl]-5-trifluoromethyl-1,2,3-thiadiazole,
  4-[4(3-amino-2-hydroxypropoxy)phenyl]-5-phenyl-1,2,3-thiadiazole and
  4-[3(3-amino-2-hydroxypropoxy)phenyl]-5-carboethoxy-1,2,3-thiadiazole.

EXAMPLE 8

To a solution of 58 g. of 4-(tetrahydropyran-2-yloxy)phenylacetaldehyde in 1160 ml. of methanol are added 32.7 g. of carbethoxyhydrazine and 0.7 ml. of glacial acetic acid, the reaction mixture is stirred at room temperature for 18 hours, and then evaporated to dryness under reduced pressure. The residue is dissolved in methylene chloride, washed with water, dried over sodium sulfate and evaporated to dryness under reduced pressure. To the oily residue (mixture of the ethoxycarbonylhydrazone of 4-(tetrahydropyran-2-yloxy) phenylacetaldehyde and ethoxycarbonylhydrazone of 4-hydroxyphenylacetaldehyde is added 150 ml. of freshly distilled thionyl chloride previously cooled to −20°C, and the reaction mixture is stirred at room temperature for 18 hours. The formed precipitate is collected by filtration, dissolved in methanol and the resulting solution decolorized with charcoal. Crystallization of the residue from methanol-water affords the pure 5-(4-hydroxyphenyl)-1,2,3-thiadiazole.

The same compound is obtained using 4-hydroxyphenylacetaldehyde as starting material.

In a similar manner, 2-(tetrahydropyran-2-yloxy) phenylacetaldehyde and 3-(tetrahydropyran-2-yloxy)-phenylacetaldehyde are converted respectively into 5-(2-hydroxyphenyl)-1,2,3-thiadiazole and 5-(3-hydroxyphenyl)-1,2,3-thiadiazole.

EXAMPLE 9

To a solution of 0.92 g. of sodium hydroxide in 425 ml. of water is added 4.1 g. of 5-(4-hydroxyphenyl)-1,2,3-thiadiazole and 5.4 ml. of epibromohydrin, stirring the reaction mixture for 20 hours at room temperature. It is then extracted with ethyl acetate, and the organic extract washed with water to neutrality, dried over sodium sulfate and evaporated to dryness under reduced pressure. The residue is chromatographed on silica gel plates using a mixture of chloroform-acetone (95:5) as eluant to yield 5-[4(2,3-epoxypropoxy)-phenyl]-1,2,3-thiadiazole. This product can be further purified by crystallization from methylene chloridehexane.

In another experiment epichlorohydrin was substituted for epibromohydrin, obtaining the same results.

Likewise, 5-(3-hydroxyphenyl)-1,2,3-thiadiazole and 5-(2-hydroxyphenyl)-1,2,3-thiadiazole are converted respectively into 5-[3(2,3-epoxypropoxy)phenyl]-1,2,3-thiadiazole and 5-[2(2,3-epoxypropoxy)phenyl]-1,2,3-thiadiazole.

EXAMPLE 10

Examples 8 and 9 are repeated using as starting material 2-methyl-2(4-tetrahydropyran-2-yloxyphenyl) acetaldehyde, to produce successively the corresponding ethoxycarbonylhydrazone (in mixture with the hydroxy derivative), 5-(4-hydroxyphenyl)-4-methyl-1,2,3-thiadiazole and 5-[4(2,3-epoxypropoxy)phenyl]-4-methyl-1,2,3-thiadiazole.

Similarly but using as starting materials the following compounds:

2-ethyl-2-(4-tetrahydropyran-2-yloxyphenyl-)acetaldehyde,
2-propyl-2-(4-tetrahydropyran-2-yloxyphenyl-)acetaldehyde,
2-isopropyl-2-(4-tetrahydropyran-2-yloxyphenyl-)acetaldehyde,
2-butyl-2-(4-tetrahydropyran-2-yloxyphenyl-)acetaldehyde,
2-methyl-2-(2-tetrahydropyran-2-yloxyphenyl-)acetaldehyde,
2-methyl-2-(3-tetrahydropyran-2-yloxyphenyl-)acetaldehyde,
2-cyano-2-(4-tetrahydropyran-2-yloxyphenyl-)acetaldehyde,
2-cyano-2-(2-tetrahydropyran-2-yloxyphenyl-)acetaldehyde,
2-cyano-2-(3-tetrahydropyran-2-yloxyphenyl-)acetaldehyde,
2-trifluoromethyl-2-(2-tetrahydropyran-2-yloxyphenyl) acetaldehyde,
2-trifluoromethyl-2-(3-tetrahydropyran-2-yloxyphenyl) acetaldehyde,
2-trifluoromethyl-2-(4-tetrahydropyran-2-yloxyphenyl) acetaldehyde,
2-phenyl-2-(2-tetrahydropyran-2-yloxyphenyl-)acetaldehyde,
2-phenyl-2-(3-tetrahydropyran-2-yloxyphenyl-)acetaldehyde, and
2-phenyl-2-(4-tetrahydropyran-2-yloxyphenyl-)acetaldehyde, there are produced as final products, respectively:
5-[4(2,3-epoxypropoxy)phenyl]-4-ethyl-1,2,3-thiadiazole,
5-[4(2,3-epoxypropoxy)phenyl]-4-propyl-1,2,3-thiadiazole,
5-[4(2,3-epoxypropoxy)phenyl]-4-isopropyl-1,2,3-thiadiazole,
5-[4(2,3-epoxypropoxy)phenyl]-4-butyl-1,2,3-thiadiazole,
5-[2(2,3-epoxypropoxy)phenyl]-4-methyl-1,2,3-thiadiazole,
5-[3(2,3-epoxypropoxy)phenyl]-4-methyl-1,2,3-thiadiazole,
5-[4(2,3-epoxypropoxy)phenyl]-4-cyano-1,2,3-thiadiazole,
5-[2(2,3-epoxypropoxy)phenyl]-4-cyano-1,2,3-thiadiazole,
5-[3(2,3-epoxypropoxy)phenyl]-4-cyano-1,2,3-thiadiazole,
5-[2(2,3-epoxypropoxy)phenyl]-4-trifluoromethyl-1,2,3-thiadiazole,
5-[3(2,3-epoxypropoxy)phenyl]-4-trifluoromethyl-1,2,3-thiadiazole,
5-[4(2,3-epoxypropoxy)phenyl]-4-trifluoromethyl-1,2,3-thiadiazole,
5-[2(2,3-epoxypropoxy)phenyl]-4-phenyl-1,2,3-thiadiazole,
5-[3(2,3-epoxypropoxy)phenyl]-4-phenyl-1,2,3-thiadiazole and
5-[4(2,3-epoxypropoxy)phenyl]-4-phenyl-1,2,3-thiadiazole.

EXAMPLE 11

To 9 g. of ethyl diazoacetate, cooled to 0°C is added 5 g. of 2-acetoxybenzoic acid chloride, and the resulting mixture is stirred at a temperature not higher than room temperature for 2 hours. It is then heated at 40°C for 18 hours and the excess reagent evaporated to dryness under vacuo. The solid residue is treated with 100 ml. of cold 5% sodium bicarbonate solution and the mixture stirred for 2 hours. It is then extracted with ether and the organic extracts washed with water, dried over sodium sulfate and evaporated to dryness under vacuo. Crystallization of the residue from acetone-ether affords the pure ethyl 4-acetoxybenzoyldiazoacetate.

A solution of 5 g. of ethyl 4-acetoxybenzoyldiazoacetate in 200 ml. of ethanol is treated with 50 ml. of aqueous 20% ammonium polysulfide solution and through the resulting mixture is passed a slow stream of hydrogen sulfide for 4 hours. The precipitate which forms is collected by filtration, dissolved in methylene chloride and filtered through a column of alkaline alumina, eluting the column with methylene chloride and methylene chloride containing increasing percentages of ether. The combined eluates are evaporated to dryness and the residue crystallized from ethyl acetatemethanol, thus obtaining the pure 5-(2-hydroxyphenyl)-4-carboethoxy-1,2,3-thiadiazole.

In a similar manner starting from 3-acetoxybenzoic acid chloride and 4-acetoxybenzoic acid chloride there are obtained, respectively, 5-(3-hydroxyphenyl)-4-carboethoxy-1,2,3-thiadiazole and 5-(4-hydroxyphenyl)-4-carboethoxy-1,2,3-thiadiazole.

Upon reaction of the above-mentioned thiadiazole compounds with epibromohydrin, in accordance with the method of Example 8, there are obtained, respectively:
5-[2(2,3-epoxypropoxy)phenyl]-4-carboethoxy-1,2,3-thiadiazole,
5-[3(2,3-epoxypropoxy)phenyl]-4-carboethoxy-1,2,3-thiadiazole, and
5-[4(2,3-epoxypropoxy)phenyl]-4-carboethoxy-1,2,3-thiadiazole.

EXAMPLE 12

A mixture of 1.5 g. of 5-[4(2,3-epoxypropoxy) phenyl]-1,2,3-thiadiazole, 45 ml. of t-butylamine and 5 ml. of t-butanol is stirred at room temperature for 96 hours. It is then evaporated to dryness under reduced pressure and the residue crystallized from methanol-ether to afford the pure 5-[4(3-t-butylamino-2-hydroxypropoxy)phenyl]-1,2,3-thiadiazole, m.p. 133°–134°C; λmax 225-226, 314 nm (ε 760, 12300) ir 3390, 3210, 1655, 1615 cm$^{-1}$.

In a similar manner, the remaining epoxypropoxy thiadiazole compounds obtained in Example 9 and the compounds of Examples 10 and 11 are converted respectively into:
5-[3(3-t-butylamino-2-hydroxypropoxy)phenyl]-1,2,3-thiadiazole,
5-[2(3-t-butylamino-2-hydroxypropoxy)phenyl]-1,2,3-thiadiazole,
5-[4(3-t-butylamino-2-hydroxypropoxy)phenyl]-4-methyl-1,2,3-thiadiazole,
5-[4(3-t-butylamino-2-hydroxypropoxy)phenyl]-4-ethyl-1,2,3-thiadiazole,
5-[4(3-t-butylamino-2-hydroxypropoxy)phenyl]-4-propyl-1,2,3-thiadiazole,
5-[4(3-t-butylamino-2-hydroxypropoxy)phenyl]-4-isopropyl-1,2,3-thiadiazole,
5-[4(3-t-butylamino-2-hydroxypropoxy)phenyl]-4-butyl-1,2,3-thiadiazole,
5-[2(3-t-butylamino-2-hydroxypropoxy)phenyl]-4-methyl-1,2,3-thiadiazole, 5-[3(3-t-butylamino-2-hydroxypropoxy)phenyl]-4-methyl-1,2,3-thiadiazole,
5-[4(3-t-butylamino-2-hydroxypropoxy)phenyl]-4-cyano-1,2,3-thiadiazole,
5-[2(3-t-butylamino-2-hydroxypropoxy)phenyl]-4-cyano-1,2,3-thiadiazole,
5-[3(3-t-butylamino-2-hydroxypropoxy)phenyl]-4-cyano-1,2,3-thiadiazole,
5-[2(3-t-butylamino-2-hydroxypropoxy)phenyl]-4-trifluoromethyl-1,2,3-thiadiazole,
5-[3(3-t-butylamino-2-hydroxypropoxy)phenyl]-4-trifluoromethyl-1,2,3-thiadiazole,
5-[4(3-t-butylamino-2-hydroxypropoxy)phenyl]-4-trifluoromethyl-1,2,3-thiadiazole,
5-[2-(3-t-butylamino-2-hydroxypropoxy)phenyl]-4-phenyl-1,2,3-thiadiazole,
5-[3(3-t-butylamino-2-hydroxypropoxy)phenyl]-4-phenyl-1,2,3-thiadiazole,
5-[4(3-t-butylamino-2-hydroxypropoxy)phenyl]-4-phenyl-1,2,3-thiadiazole,
5-[2(3-t-butylamino-2-hydroxypropoxy)phenyl]-4-carboethoxy-1,2,3-thiadiazole,
5-[3(3-t-butylamino-2-hydroxypropoxy)phenyl]-4-carboethoxy-1,2,3-thiadiazole, and
5-[4(3-t-butylamino-2-hydroxypropoxy)phenyl]-4-carboethoxy-1,2,3-thiadiazole.

EXAMPLE 13

To a solution of 10 g. of 4-(2-hydroxyphenyl)5-carboethoxy-1,2,3-thiadiazole in 500 ml. of ethanol is added a solution of 5 g. of sodium hydroxide in 25 ml. of water. The reaction mixture is refluxed for 4 hours and then evaporated to a small volume under vacuo. It is then cooled, diluted with water and extracted with ether to eliminate unsaponifiable products. The aqueous phase is acidified with 10% hydrochloric acid solution and extracted with ethyl acetate. The combined ethyl acetate extracts are washed with sodium chloride solution, dried over sodium sulfate and evaporated to dryness under vacuo. Crystallization of the residue from ethyl acetate-methanol, affords the pure 4-(2-hydroxyphenyl)5-carboxy-1,2,3-thiadiazole.

A mixture of 22.2 g. of 4-(2-hydroxyphenyl)-5carboxy-1,2,3-thiadiazole, 10.1 g. of anhydrous triethylamine, 150 ml. of anhydrous toluene and 50 ml. of anhydrous ether is cooled to 0°C and treated dropwise with 10.8 g. (0.1 mol) of ethyl chlorocarbonate previously cooled to 0°C, maintaining the temperature of the reaction mixture at about 0°C. The reaction mixture is stirred at the same temperature for 30 minutes further and then a cold solution of 4.5 g. of dimethylamine in 10 ml. of anhydrous ether is added in a dropwise fashion. The resulting mixture is stirred for 30 minutes further at 0°C and then allowed to stand at room temperature for 18 hours. The triethylamine hydrochloride formed is then separated by filtration. The filtrate is washed with dilute hydrochloric acid solution, sodium bicarbonate solution and water to neutrality, dried over sodium sulfate and evaporated to dryness under vacuo. The residue is dissolved in 200 ml. of methanol, 10.6 g. of sodium carbonate dissolved in 20 ml. of water are then added and the reaction mixture is stirred at room temperature for 1 hour. It is then neutralized with dilute hydrochloric acid solution, concentrated to a small volume under reduced pressure, diluted with ice water and extracted with ethyl acetate. The combined extracts are washed with water to neutrality, dried over sodium sulfate and evaporated to dryness under vacuo. The residue is purified by chromatography, to yield 4-(2-hydroxyphenyl-5-dimethylaminocarbonyl-1,2,3-thiadiazole.

In a similar manner, starting from
4-(3-hydroxyphenyl)-5-carboethoxy-1,2,3-thiadiazole,
4-(4-hydroxyphenyl)-5-carboethoxy-1,2,3-thiadiazole,
5-(2-hydroxyphenyl)-4-carboethoxy-1,2,3-thiadiazole,
5-(3-hydroxyphenyl)-4-carboethoxy-1,2,3-thiadiazole and
5-(4-hydroxyphenyl)-4-carboethoxy-1,2,3-thiadiazole there are respectively obtained:
4-(3-hydroxyphenyl)-5-dimethylaminocarbonyl-1,2,3-thiadiazole,
4-(4-hydroxyphenyl)-5-dimethylaminocarbonyl-1,2,3-thiadiazole,
5-(2-hydroxyphenyl)-4-dimethylaminocarbonyl-1,2,3-thiadiazole,
5-(3-hydroxyphenyl)-4-dimethylaminocarbonyl-1,2,3-thiadiazole and
5-(4-hydroxyphenyl)-4-dimethylaminocarbonyl-1,2,3-thiadiazole.

In a similar manner but using equivalent amounts of methylamine, diethylamine, isopropylamine, n-butylamine, 4-methylhexylamine and 5-methylhexylamine in place of dimethylamine, there are obtained the corresponding monoalkyl- or dialkylaminocarbonyl derivatives, e.g.,
4-(2-hydroxyphenyl)-5-methylaminocarbonyl-1,2,3-thiadiazole,
4-(3-hydroxyphenyl)-5-diethylaminocarbonyl-1,2,3-thiadiazole,
4-(4-hydroxyphenyl)-5-isopropylaminocarbonyl-1,2,3-thiadiazole,
5-(2-hydroxyphenyl)-4-diethylaminocarbonyl-1,2,3-thiadiazole,
5-(3-hydroxyphenyl)-4-n-butylaminocarbonyl-1,2,3-thiadiazole,
5-(4-hydroxyphenyl)-4-methylaminocarbonyl-1,2,3-thiadiazole,
5-(4-hydroxyphenyl)-4-(4-methylhexylaminocarbonyl)-1,2,3-thiadiazole, and
5-(4-hydroxyphenyl)-4-(5-methylhexylaminocarbonyl)-1,2,3-thiadiazole.

In some cases, the aminocarbonyl compound precipitates from the reaction mixture together with the triethylamine hydrochloride. In those cases, the precipitate is washed with dilute sodium hydroxide solution, dilute hydrochloric acid and water. The solid aminocarbonyl compound is air dried, dissolved in methanol and treated with sodium carbonate as previously mentioned.

EXAMPLE 14

By following the methods of Examples 4 and 5 (parts A or B), 4-(2-hydroxyphenyl)-5-dimethylaminocarbonyl-1,2,3-thiadiazole is converted into 4-[2(3-t-butylamino-2-hydroxypropoxy)phenyl]-5-dimethylaminocarbonyl-1,2,3-thiadiazole via the epoxypropoxy intermediate.

In a similar manner, the remaining compounds obtained in Example 13 produce as final products, respectively:
4-[3(3-t-butylamino-2-hydroxypropoxy)phenyl]-5-dimethylaminocarbonyl-1,2,3-thiadiazole, 4-[4(3-t-butylamino-2-hydroxypropoxy)phenyl]-5-dimethylaminocarbonyl-1,2,3-thiadiazole, 5-[2(3-t-butylamino-2-hydroxypropoxy)phenyl]-4-dimethylaminocarbonyl-1,2,3-thiadiazole, 5-[3(3-t-butylamino-2-hydroxypropoxy)phenyl]-4-dimethylaminocarbonyl-1,2,3-thiadiazole, 5-[4(3-t-butylamino-2-hydroxypropoxy)phenyl]-4-dimethylaminocarbonyl-1,2,3-thiadiazole, 4-[2(3-t-butylamino-2-hydroxypropoxy)phenyl]-5-methylaminocarbonyl-1,2,3-thiadiazole, 4-[3(3-t-butylamino-2-hydroxpropoxy)phenyl]-5-diethylaminocarbonyl-1,2,3-thiadiazole, 4-[4(3-t-butylamino-2-hydroxypropoxy)phenyl]-5-isopropylaminocarbonyl-1,2,3-thiadiazole, 5-[2(3-t-butylamino-2-hydroxypropoxy)phenyl]-4-diethylaminocarbonyl-1,2,3-thiadiazole, 5-[3(3-t-butylamino-2-hydroxypropoxy)phenyl]-4-n-butylaminocarbonyl-1,2,3-thiadiazole, 5-[4(3-t-butylamino-2-hydroxypropoxy)phenyl]-4-methylaminocarbonyl-1,2,3-thiadiazole, 5-[4(3-t-butylamino-2-hydroxypropoxy)phenyl]-4-(4-methylhexylaminocarbonyl)-1,2,3-thiadiazole, and 5-[4(3-t-butylamino-2-hydroxypropoxy)phenyl]-4-(5-methylhexylaminocarbonyl)-1,2,3-thiadiazole.

EXAMPLE 15

By following the method of Example 6, part B, 500 mg. of 5-[2(2,3-epoxypropoxy)phenyl]-1,2,3-thiadiazole is converted into 5-[2{3(4-carbamoyl-phenoxyethylamino)-2-hydroxypropoxy} phenyl]-1,2,3-thiadiazole.

Likewise, the remaining epoxypropoxy thiadiazole compounds of Example 9 and the compounds of Examples 10 and 11 can be converted into the corresponding carbamoylphenoxyethylamino hydroxypropoxy derivatives. Representative compounds thus obtained are:

5-[4{3(4-carbamoylphenoxyethylamino)2-hydroxypropoxy}phenyl]-1,2,3-thiadiazole,

5-[2{3(4-carbamoylphenoxyethylamino)-2-hydroxypropoxy} phenyl]-4-methyl-1,2,3-thiadiazole, 5-[4{3(4-carbamoylphenoxyethylamino)-2-hydroxypropoxy} phenyl]-4-ethyl-1,2,3-thiadiazole, 5-[3{3(4-carbamoylphenoxyethylamino)-2-hydroxypropoxy} phenyl]-4-cyano-1,2,3-thiadiazole, 5-[4{3(4-carbamoylphenoxyethylamino)-2-hydroxypropoxy} phenyl]-4-phenyl-1,2,3-thiadiazole, 5-[2{3(4-carbamoylphenoxyethylamino)-2-hydroxypropoxy} phenyl]-4-trifluoromethyl-1,2,3-thiadiazole and 4-[4{3(4-carbamoylphenoxyethylamino)-2-hydroxypropoxy}phenyl]-4-carboethoxy-1,2,3-thiadiazole.

EXAMPLE 16

To a solution of 200 mg. of 4-[4(2,3-epoxypropoxy)-phenyl]-1,2,3-thiadiazole in 10 ml. of anhydrous ethanol is added 0.4 g. of methylamine and the resulting mixture is allowed to stand at room temperature. The course of the reaction is followed by thin layer chromatographic analysis of aliquots taken at periodical intervals. When the transformation of the starting compound is essentially complete the solvent and excess reagent are eliminated under vacuum distillation and the residue purified by recrystallization from acetone-ether, thus obtaining 4-[4(3-methylamino-2-hydroxypropoxy)phenyl]-1,2,3-thiadiazole in pure form.

In a similar manner, starting from 5-[2(2,3-epoxypropoxy)phenyl]-1,2,3-thiadiazole there is obtained 5-[2(3-methylamino-2-hydroxypropoxy)phenyl]-1,2,3-thiadiazole.

EXAMPLE 17

A mixture of 10 g. of isopropylamine, 2 g. of 4-[4(2,3-epoxypropoxy)phenyl]-1,2,3-thiadiazole and 10 ml. of isopropanol is refluxed under stirring for 6 hours. The isopropanol and unreacted isopropylamine are then removed by distillation under vacuo. Crystallization of the residue from methanol-ether produces the pure 4-[4(3-isopropylamino-2hydroxypropoxy)-phenyl]-1,2,3-thiadiazole.

In a similar manner from the corresponding 2,3-epoxypropoxyphenyl thiadiazole compounds, there are obtained:

4-[3(3-isopropylamino-2-hydroxypropoxy)phenyl]-1,2,3-thiadiazole,

4-[2(3-isopropylamino-2-hydroxypropoxy)phenyl]-1,2,3-thiadiazole,

4-[4(3-isopropylamino-2-hydroxypropoxy)phenyl]-5-methyl1,2,3-thiadiazole,

4-[3(3-isopropylamine-2-hydroxypropoxy)phenyl]-5-cyano-1,2,3-thiadiazole,

4-[2(3-isopropylamino-2-hydroxypropoxy)phenyl]-5-trifluoromethyl-1,2,3-thiadiazole, 5-[4(3-isopropylamino-2-hydroxypropoxy)phenyl]-1,2,3-thiadiazole, 5-[2(3-isopropylamino-2-hydroxypropoxy)phenyl]-1,2,3-thiadiazole, 5-[4(3-isopropylamino-2-hydroxypropoxy)phenyl]-4-methyl-1,2,3-thiadiazole, 5-[4(3-isopropylamino-2-hydroxypropoxy)phenyl]-4-ethyl-1,2,3-thiadiazole, 5-[2(3-isopropylamino-2-hydroxypropoxy)phenyl]-4-phenyl-1,2,3-thiadiazole, and 5-[4(3-isopropylamino-2-hydroxypropoxy)phenyl]-4-carboethoxy-1,2,3-thiadiazole.

EXAMPLE 18

By following the methods of Example 5 or 17 using 4-[4(2,3-epoxypropoxy)phenyl]-1,2,3-thiadiazole as starting material and ethylamine, cyclopropylamine, benzylamine, phenethylamine, cyclopentylamine and α-phenylpropylamine as reagents in place of t-butylamine or isopropylamine, respectively, there are obtained the corresponding amino derivatives, namely:

4-[4(3-ethylamino-2-hydroxypropoxy)phenyl]-1,2,3-thiadiazole,

4-[4(3-cyclopropylamino-2-hydroxypropoxy)-phenyl]-1,2,3-thiadiazole,

4-[4(3-cyclopentylamino-2-hydroxypropoxy)-phenyl]-1,2,3-thiadiazole,

4-[4(3-benzylamino-2-hydroxypropoxy)phenyl]-1,2,3-thiadiazole,

4-[4(3-phenethylamino-2-hydroxypropoxy)phenyl]-1,2,3-thiadiazole and

4-[4(3-γ-phenylpropylamino-2-hydroxypropoxy)-phenyl]-1,2,3-thiadiazole.

Likewise but using 5-[4(2,3-epoxypropoxy)phenyl]-1,2,3-thiadiazole as starting material there are respectively produced:

5-[4(3-ethylamino-2-hydroxypropoxy)phenyl]-1,2,3-thiadiazole,

5-[4(3-cyclopropylamino-2-hydroxypropoxy)-phenyl]-1,2,3-thiadiazole,

5-[4(3-cyclopentylamino-2-hydroxypropoxy)-phenyl]-1,2,3-thiadiazole,

5-[4(3-benzylamino-2-hydroxypropoxy)phenyl]-1,2,3-thiadiazole,
5-[4(3-phenethylamino-2-hydroxypropoxy)phenyl]-1,2,3-thiadiazole and
5-[4(3-γ-phenylpropylamino-2-hydroxypropoxy)-phenyl]-1,2,3-thiadiazole.

EXAMPLE 19

A mixture of 4.5 g. of 4-(2-hydroxyphenyl)-5-carboxy-1,2,3-thiadiazole, obtained as described in Example 13, 45 ml. of methanol and 2 ml. of concentrated hydrochloric acid is refluxed for 18 hours. It is then poured into water, the resultant precipitate collected by filtration and washed with sodium carbonate solution and water, dried and recrystallized from methylene chloride-ether to give 4-(2-hydroxyphenyl)-5methoxycarbonyl-1,2,3-thiadiazole.

The foregoing procedure is repeated using propanol and isopropanol in place of methanol, obtaining respectively 4-(2-hydroxyphenyl)-5-propoxycarbonyl-1,2,3-thiadiazole and 4-(2-hydroxyphenyl)-5-isopropoxycarbonyl-1,2,3-thiadiazole.

Upon reaction of the above mentioned compounds with epibromohydrin in the presence of sodium hydroxide, in accordance with the method of Example 4 there are produced the corresponding epoxypropoxy derivatives, which are in turn treated with t-butylamine, by the methods described in parts A or B of Example 5, to yield as final products:
 4-[2(3-t-butylamino-2-hydroxypropoxy)phenyl]-5-methoxycarbonyl-1,2,3-thiadiazole,
 4-[2(3-t-butylamino-2-hydroxypropoxy)phenyl]-5-propoxycarbonyl-1,2,3-thiadiazole and
 4-[2(3t-butylamino-2-hydroxypropoxy)phenyl]-5-isopropoxycarbonyl-1,2,3-thiadiazole.

EXAMPLE 20

To a solution of 200 mg. of 4-[4(3-t-butylamino-2-hydroxypropoxy)phenyl]-5-carboethoxy-1,2,3-thiadiazole in 15 ml. of methanol is added a solution of 100 mg. of sodium hydroxide in 2 ml. of water, and the reaction mixture is refluxed for 4 hours. It is then cooled, evaporated to a small volume under vacuo, diluted with 25 ml. of water and extracted with ethyl acetate to eliminate the unsaponified product. The aqueous phase is passed through a column of 10 g. of ion exchange resin sold by the Dow Chemical Company under the trademark Dowex 50, acidic type (H$^+$) eluting the column first with water and thereafter with 10% acetic acid solution. The combined acidic eluates are concentrated to a small volume under reduced pressure at low temperature and then lyophilized, to yield 4-[4(3-t-butylamino-2-hydroxypropoxy)phenyl]-5-carboxy-1,2,3-thiadiazole.

The foregoing compound is then esterified with methanol in the presence of hydrochloric acid, in accordance with the method of Example 19, to yield 4-[4(3-t-butylamino-2-hydroxypropoxy)phenyl]-5-methoxycarbonyl-1,2,3-thiadiazole hydrochloride, which upon neutralization with 10% sodium carbonate solution affords the free amino derivative, 4-[4(3-t-butylamino-2-hydroxypropoxy)phenyl]-5-methoxycarbonyl-1,2,3-thiadiazole.

In a similar manner but using 5-[4(3-t-butylamino-2-hydroxypropoxy)phenyl]-4-carboethoxy-1,2,3-thiadiazole as starting material there are successively obtained 5-[4(3-t-butylamino-2-hydroxypropoxy)-phenyl]-4-carboxy-1,2,3-thiadiazole, 5-[4(3-t-butylamino-2-hydroxypropoxy)phenyl]-4-methoxycarbonyl-1,2,3-thiadiazole hydrochloride and 5-[4(3-t-butylamino-2-hydroxypropoxy)phenyl]-4-methoxycarbonyl-1,2,3-thiadiazole.

EXAMPLE 21

To a solution of 80 mg. of sodium hydroxide in 10 ml. of water is added 250 mg. of 4-(4-hydroxyphenyl)-5-carboxy-1,2,3-thiadiazole. The reaction mixture is stirred for 10 minutes and then treated dropwise with 0.4 ml. of epibromohydrin, maintaining the reaction mixture at room temperature under stirring for 48 additional hours. It is then acidified with 10% hydrochloric acid solution and extracted with ethyl acetate. The combined organic extracts are dried over sodium sulfate and evaporated to dryness under reduced pressure. Crystallization of the residue from chloroformmethanol affords the pure 4-[4(2,3-epoxypropoxy)-phenyl]-5-carboxy-1,2,3-thiadiazole.

The foregoing compound is then treated with methyl iodide in the presence of lithium carbonate and thereafter with isopropylamine in accordance with the methods of Examples 19 and 17, respectively, to produce 4-[4(3-isopropylamino-2-hydroxypropoxy)phenyl]-5-carbomethoxy-1,2,3-thiadiazole.

EXAMPLE 22

A solution of 1 g. of 4-[4(3-t-butylamino-2-hydroxypropoxy)phenyl]-1,2,3-thiadiazole in 50 ml. of absolute ethanol is treated with 10 ml. of 4N alcoholic hydrochloric acid. After 10 minutes at room temperature, the solution is diluted with anhydrous diethyl ether. The precipitate which forms is separated by filtration, washed with ether and recrystallized from ethanol-diethyl ether, thus obtaining 4-[4(3-t-butylamino-2-hydroxypropoxy)phenyl]-1,2,3-thiadiazole hydrochloride.

In a similar manner, the other aminohydroxypropoxyphenyl thiadiazole compounds obtained in the previous Examples can be converted into the corresponding hydrochloride acid addition salts.

Representative compounds thus obtained are:
 4-[3(3-t-butylamino-2-hydroxypropoxy)phenyl]-1,2,3-thiadiazole hydrochloride,
 4-[2(3-isopropylamino-2-hydroxypropoxy)phenyl]-1,2,3-thiadiazole hydrochloride,
 4-[4(3-t-butylamino-2-hydroxypropoxy)phenyl]-5-methyl-1,2,3-thiadiazole hydrochloride,
 4-[2(3-t-butylamino-2-hydroxypropoxy)phenyl]-5-cyano-1,2,3-thiadiazole hydrochloride,
 4-[4(3-t-butylamino-2-hydroxypropoxy)phenyl]-5-trifluoromethyl-1,2,3-thiadiazole hydrochloride,
 4-[4(3-isopropylamino-2-hydroxypropoxy)phenyl]-1,2,3-thiadiazole hydrochloride,
 4-[4(3-cyclopropylamino-2-hydroxypropoxy)-phenyl]-1,2,3-thiadiazole hydrochloride,
 5-[4(3-t-butylamino-2-hydroxypropoxy)phenyl]-1,2,3-thiadiazole hydrochloride,
 5-[3(3-t-butylamino-2-hydroxypropoxy)phenyl]-1,2,3-thiadiazole hydrochloride,
 5-[2(3-t-butylamino-2-hydroxypropoxy)phenyl]-1,2,3-thiadiazole hydrochloride,
 5-[4(3-benzylamino-2-hydroxypropoxy)phenyl]-1,2,3-thiadiazole hydrochloride,
 5-[2(3-t-butylamino-2-hydroxypropoxy)phenyl]-4-dimethylaminocarbonyl-1,2,3-thiadiazole hydrochloride, 5-[4(3-t-butylamino-2-hydroxypropoxy)phenyl]-4-ethyl-1,2,3-thiadiazole hydrochloride,
5-[4(3-t-butylamino-2-hydroxypropoxy)phenyl]-4-carboethoxy-1,2,3-thiadiazole hydrochloride,
5-[2(3-t-butylamino-2-hydroxypropoxy)phenyl]-4-phenyl-1,2,3-thiadiazole hydrochloride,
4-[4{3-(carbamoylphenoxyethylamino)-2-hydroxypropoxy}phenyl]-1,2,3-thiadiazole hydrochloride,
4-[2{3-(carbamoylphenoxyethylamino)-2-hydroxypropoxy}phenyl]-1,2,3-thiadiazole hydrochloride,
5-[4{3-(carbamoylphenoxyethylamino)-2-hydroxypropoxy}phenyl]-1,2,3-thiadiazole hydrochloride, and
5-[2{3-(carbamoylphenoxyethylamino)-2-hydroxypropoxy}phenyl]-4-methyl-1,2,3-thiadiazole hydrochloride.

EXAMPLE 23

One gram of 4-[4(3-t-butylamino-2-hydroxypropoxy)phenyl]-1,2,3-thiadiazole is dissolved in a mixture of 5 ml. of diethyl ether and 5 ml. of ethanol at 20°C. To this solution is added 10 ml. of a saturated solution of maleic acid in diethyl ether. The mixture is allowed to stand for 1 hour at room temperature. The resulting precipitate is separated by filtration, washed three times with diethyl ether and then crystallized from ethyl acetate-ether affording the pure 4-[4(3-t-butylamino-2-hydroxypropoxy)phenyl]-1,2,3-thiadiazole maleate salt.

Similarly by following the same procedure using each of the compounds of formulas (A) and (B) enumerated in Examples 5, 6, 7, 12, 14, 15, 16, 17, 18, 19 and 20, as starting materials, the corresponding maleate addition salts of each of these compounds is respectively prepared.

Obviously many modifications and variations of the invention, described herein above and in the Claims, can be made without departing from the essence and scope thereof.

We claim:

1. A compound selected from the group of those represented by the following formulas:

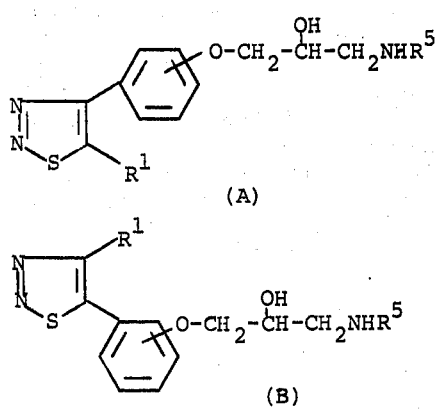

wherein
R$^1$ is selected from the group consisting of hydrogen, lower alkyl, phenyl, trifluoromethyl, carboxy, lower alkoxycarbonyl, cyano and an unsubstituted, monosubstituted or disubstituted aminocarbonyl group of the formula CONR$^3$R$^4$, wherein each of R$^3$ and R$^4$ is independently hydrogen, alkyl having 1 through 8 carbon atoms, phenyl or phenyl lower alkyl;
R$^5$ is hydrogen, lower alkyl, cyclomethylene containing from 3 to 7 carbon atoms, phenyl, phenyl lower alkyl, or the group

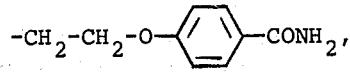

and the group

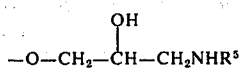

can be situated at the ortho-, meta- or para- positions with respect to the thiadiazole ring, and pharmaceutically acceptable acid addition salts thereof.

2. A compound according to claim 1 wherein the group

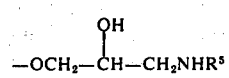

is situated at the para- position with respect to the thiadiazole ring.

3. A compound according to claim 1 wherein the group

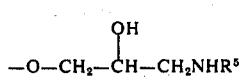

is situated at the ortho- position with respect to the thiadiazole ring.

4. A compound according to claim 1 wherein the group —O—CH$_2$—CH—CH$_2$NHR$^5$ is situated at the meta- position with respect to the thiadiazole ring.

5. A compound according to claim 1 wherein R$^5$ is t-butyl.

6. A compound according to claim 1 wherein R$^5$ is isopropyl.

7. A compound according to claim 1 wherein R$^5$ is the group

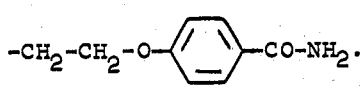

8. A compound according to claim 1 wherein R$^1$ is hydrogen.

9. A compound according to claim 1 wherein R$^1$ is lower alkyl.

10. A compound according to claim 1 wherein R$^1$ is phenyl.

11. A compound according to claim 1 wherein R$^1$ is trifluoromethyl.

12. A compound according to claim 1 wherein R$^1$ is carboxy.

13. A compound according to claim 1 wherein R$^1$ is lower alkoxycarbonyl.

14. A compound according to claim 1 wherein R$^1$ is the group CONR$^3$R$^4$.

15. A compound according to claim 1 formula (A) and the pharmaceutically acceptable acid addition salts thereof.

16. A compound according to claim 15 wherein said compound is 4-[4(3-t-butylamino-2-hydroxypropoxy)phenyl]1,2,3-thiadiazole and the pharmaceutically acceptable acid addition salts thereof.

17. A compound according to claim 15 wherein said compound is 4-[3(3-t-butylamino-2-hydroxypropoxy)- phenyl]1,2,3-thiadiazole and the pharmaceutically acceptable acid addition salts thereof.

18. A compound according to claim 15 wherein said compound is 4-[2(3-t-butylamino-2-hydroxypropoxy)-phenyl]1,2,3-thiadiazole and the pharmaceutically acceptable acid addition salts thereof.

19. A compound according to claim 15 wherein said compound is 4-[4(3-isopropylamino-2-hydroxypropoxy)phenyl]1,2,3-thiadiazole and the pharmaceutically acceptable acid addition salts thereof.

20. A compound according to claim 15 wherein said compound is 4-[3(3-isopropylamino-2-hydroxypropoxy)phenyl]1,2,3-thiadiazole and the pharmaceutically acceptable acid addition salts thereof.

21. A compound according to claim 15 wherein said compound is 4-[2(3-isopropylamino-2-hydroxypropoxy)phenyl]-1,2,3-thiadiazole and the pharmaceutically acceptable acid addition salts thereof.

22. A compound according to claim 15 wherein said compound is 4-[4{3-(4-carbamoylphenoxyethylamino)-2-hydroxypropoxy}phenyl]-1,2,3-thiadiazole and the pharmaceutically acceptable acid addition salts thereof.

23. A compound according to claim 15 wherein said compound is 4-[3{3-(4-carbamoylphenoxyethylamino)-2-hydroxypropoxy}phenyl]-1,2,3-thiadiazole and the pharmaceutically acceptable acid addition salts thereof.

24. A compound according to claim 15 wherein said compound is 4-[2{3-(4-carbamoylphenoxyethylamino)-2-hydroxypropoxy}phenyl]-1,2,3-thiadiazole and the pharmaceutically acceptable acid addition salts thereof.

25. A compound according to claim 15 wherein said compound is 4-[4(3-t-butylamino-2-hydroxypropoxy)-phenyl]-5-methyl-1,2,3-thiadiazole and the pharmaceutically acceptable acid addition salts thereof.

26. A compound according to claim 15 wherein said compound is 4-[4(3-isopropylamino-2-hydroxypropoxy)phenyl]-5-methyl-1,2,3-thiadiazole and the pharmaceutically acceptable acid addition salts thereof.

27. A compound according to claim 15 wherein said compound is 4-[4{3(4-carbamoylphenoxyethylamino)-2-hydroxypropoxy}phenyl]-5-methyl-1,2,3-thiadiazole and the pharmaceutically acceptable acid addition salts thereof.

28. A compound according to claim 1, formula (B) and the pharmaceutically acceptable acid addition salts thereof.

29. A compound according to claim 28 wherein said compound is 5-[4(3-t-butylamino-2-hydroxypropoxy)-phenyl]-1,2,3-thiadiazole and the pharmaceutically acceptable acid addition salts thereof.

30. A compound according to claim 28 wherein said compound is 5-[3(3-t-butylamino-2-hydroxypropoxy)-phenyl]-1,2,3-thiadiazole and the pharmaceutically acceptable acid addition salts thereof.

31. A compound according to claim 28 wherein said compound is 5-[2(3-t-butylamino-2-hydroxypropoxy)-phenyl]-1,2,3-thiadiazole and the pharmaceutically acceptable acid addition salts thereof.

32. A compound according to claim 28 wherein said compound is 5-[4(3-isopropylamino-2-hydroxypropoxy)phenyl]-1,2,3-thiadiazole and the pharmaceutically acceptable acid addition salts thereof.

33. A compound according to claim 28 wherein said compound is 5-[3(3-isopropylamino-2-hydroxypropoxy)phenyl]-1,2,3-thiadiazole and the pharmaceutically acceptable acid addition salts thereof.

34. A compound according to claim 28 wherein said compound is 5-[2(3-isopropylamino-2-hydroxypropoxy)phenyl]-1,2,3-thiadiazole and the pharmaceutically acceptable acid addition salts thereof.

35. A compound according to claim 28 wherein said compound is 5-[4{3-(4-carbamoylphenoxyethylamino)-2-hydroxypropoxy}phenyl]-1,2,3-thiadiazole and the pharmaceutically acceptable acid addition salts thereof.

36. A compound according to claim 28 wherein said compound is 5-[3{3-(4-carbamoylphenoxyethylamino)-2-hydroxypropoxy}phenyl]-1,2,3-thiadiazole and the pharmaceutically acceptable acid addition salts thereof.

37. A compound according to claim 28 wherein said compound is 5-[2{3-(4-carbamoylphenoxyethylamino)-2-hydroxypropoxy}phenyl]-1,2,3-thiadiazole and the pharmaceutically acceptable acid addition salts thereof.

38. A compound according to claim 28 wherein said compound is 5-[4(3-t-butylamino-2-hydroxypropoxy)-phenyl]-4-methyl-1,2,3-thiadiazole and the pharmaceutically acceptable acid addition salts thereof.

39. A compound according to claim 28 wherein said compound is 5-[4(3-isopropylamino-2-hydroxypropoxy)phenyl]-4-methyl-1,2,3-thiadiazole and the pharmaceutically acceptable acid addition salts thereof.

40. A compound according to claim 28 wherein said compound is 5-[4{3(4-carbamoylphenoxyethylamino)-2-hydroxypropoxy}phenyl]-4-methyl-1,2,3-thiadiazole and the pharmaceutically acceptable acid addition salts thereof.

41. The compound of claim 1 wherein said cyclomethylene is selected from the group consisting of cyclopropyl, cyclopentyl, cyclohexyl, and cycloheptyl.

* * * * *